United States Patent
Uchiyama et al.

(10) Patent No.: US 11,427,523 B2
(45) Date of Patent: Aug. 30, 2022

(54) BISPHENOL COMPOSITION CONTAINING AROMATIC ALCOHOL SULFONATE AND METHOD FOR PRODUCING SAME, POLYCARBONATE RESIN AND METHOD FOR PRODUCING SAME, AND BISPHENOL PRODUCTION METHOD

(71) Applicant: MITSUBISHI CHEMICAL CORPORATION, Chiyoda-ku (JP)

(72) Inventors: Kei Uchiyama, Chiyoda-ku (JP); Takayuki Yoshida, Chiyoda-ku (JP); Rie Konishi, Chiyoda-ku (JP); Kazuo Hirowatari, Chiyoda-ku (JP); Takaharu Oono, Chiyoda-ku (JP)

(73) Assignee: MITSUBISHI CHEMICAL CORPORATION, Chiyoda-ku (JP)

( * ) Notice: Subject to any disclaimer, the term of this patent is extended or adjusted under 35 U.S.C. 154(b) by 0 days.

(21) Appl. No.: 16/797,098

(22) Filed: Feb. 21, 2020

(65) Prior Publication Data

US 2020/0190004 A1 Jun. 18, 2020

Related U.S. Application Data

(63) Continuation of application No. PCT/JP2018/031033, filed on Aug. 22, 2018.

(30) Foreign Application Priority Data

Aug. 22, 2017 (JP) .............................. JP2017-159687
Dec. 6, 2017 (JP) .............................. JP2017-234313

(51) Int. Cl.
| | | |
|---|---|---|
| C07C 37/20 | (2006.01) | |
| C07C 39/16 | (2006.01) | |
| C07C 39/17 | (2006.01) | |
| C07C 37/68 | (2006.01) | |
| C08G 64/20 | (2006.01) | |
| B01J 27/053 | (2006.01) | |

(52) U.S. Cl.
CPC .......... C07C 37/685 (2013.01); B01J 27/053 (2013.01); C07C 37/20 (2013.01); C07C 39/16 (2013.01); C07C 39/17 (2013.01); C08G 64/20 (2013.01); C07C 2527/053 (2013.01)

(58) Field of Classification Search
CPC ...................................................... C07C 39/16
See application file for complete search history.

(56) References Cited

U.S. PATENT DOCUMENTS

| | | |
|---|---|---|
| 5,763,686 A | 6/1998 | McCloskey et al. |
| 2010/0121018 A1* | 5/2010 | Yoshida ................. C08G 64/06 528/190 |
| 2012/0232240 A1 | 9/2012 | Hyodo et al. |

FOREIGN PATENT DOCUMENTS

| | | |
|---|---|---|
| JP | 62-138443 A | 6/1987 |
| JP | 06-135875 A | 5/1994 |
| JP | 10-045649 A | 2/1998 |
| JP | 10-236998 | 9/1998 |
| JP | 2000-239204 A | 9/2000 |
| JP | 2003-221352 A | 8/2003 |
| JP | 2006-36685 A | 2/2006 |
| JP | 2006-124331 A | 5/2006 |
| JP | 2007-99741 A | 4/2007 |
| JP | 2008-115139 A | 5/2008 |
| JP | 2008-214248 A | 9/2008 |
| JP | 2009-161438 A | 7/2009 |
| JP | 2014-40376 A | 3/2014 |
| JP | 2015-51935 A | 3/2015 |
| JP | 2018-145176 A | 9/2018 |
| JP | 2018-145177 A | 9/2018 |
| JP | 2018-145178 A | 9/2018 |
| WO | WO 2011/049021 A1 | 4/2011 |

OTHER PUBLICATIONS

English translation of Patent No. JP2018145178A, Published Aug. 20, 2018, pp. 1-9 (Year: 2018).*
Extended European Search Report dated Jul. 10, 2020 in European Patent Application No. 18848469.5, 9 pages.
International Search Report dated Oct. 30, 2018 in PCT/JP2018/031033, 2 pages.
International Preliminary Report on Patentability and Written Opinion dated Mar. 5, 2020 in PCT/JP2018/031033 (English Translation only), 10 pages.
Norimitsu Shimanouchi, "Synthesis of Bisphenol A", Journal of the Chemical Society of Japan, Nippon Kagaku Kaishi, No. 8, 1982, (with English Translation),( pp. 1363-1370), 27 pages.
Indian First Examination dated Jul. 19, 2021, in Indian Patent Application No. 202017011921.

(Continued)

*Primary Examiner* — Medhanit W Bahta
(74) *Attorney, Agent, or Firm* — Oblon, McClelland, Maier & Neustadt, L.L.P.

(57) ABSTRACT

A bisphenol composition including a specific amount of aromatic alcohol sulfonate, and a simple method of producing it are provided. Also provided is a method of producing a polycarbonate resin in which, by using the bisphenol composition including a specific amount of aromatic alcohol sulfonate, melt polymerization reaction can be efficiently allowed to proceed to produce a polycarbonate resin having an excellent color tone. A bisphenol composition including an aromatic alcohol sulfonate at not less than 0.1 ppb by mass with respect to a bisphenol. A method of producing a bisphenol composition, including reacting a ketone or an aldehyde with an aromatic alcohol in the presence of sulfuric acid to produce a bisphenol composition. A method of producing a polycarbonate resin, including producing a polycarbonate resin using the bisphenol composition. A polycarbonate resin including a specific amount of aromatic alcohol sulfonate.

16 Claims, No Drawings

(56) References Cited

OTHER PUBLICATIONS

Office Action dated Mar. 22, 2022 in corresponding Japanese Patent Application No. 2019-537662 (with English Translation), 12 pages.
Combined Chinese Office Action and Search Report dated Mar. 7, 2022 in Chinese Patent Application No. 201880054377.1 (with English translation), 16 pages.

\* cited by examiner

BISPHENOL COMPOSITION CONTAINING AROMATIC ALCOHOL SULFONATE AND METHOD FOR PRODUCING SAME, POLYCARBONATE RESIN AND METHOD FOR PRODUCING SAME, AND BISPHENOL PRODUCTION METHOD

CROSS-REFERENCE TO RELATED APPLICATION

This is a continuation of International Application PCT/JP2018/031033, filed on Aug. 22, 2018, and designated the U.S., and claims priority from Japanese Patent Application 2017-159687 which was filed on Aug. 22, 2017, and Japanese Patent Application 2017-234313 which was filed on Dec. 6, 2017, the entire contents of which are incorporated herein by reference.

TECHNICAL FIELD

The present invention relates to a bisphenol composition containing an aromatic alcohol sulfonate, and a method of producing it. The present invention also relates to a method of producing a polycarbonate resin using the bisphenol composition. The present invention also relates to a polycarbonate resin containing an aromatic alcohol sulfonate. The present invention also relates to a method of producing a bisphenol, comprising producing a bisphenol from reaction of an aromatic alcohol with a ketone or an aldehyde.

The bisphenol composition as one embodiment of the present invention is useful as resin raw materials such as polycarbonate resins, epoxy resins, and aromatic polyester resins; and additives such as curing agents, developers, discoloration inhibitors, microbicides, and antibacterial/antifungal agents.

BACKGROUND ART

Bisphenols are useful as raw materials of polymer materials such as polycarbonate resins, epoxy resins, and aromatic polyester resins. Known representative examples of bisphenols include 2,2-bis(4-hydroxyphenyl)propane and 2,2-bis(4-hydroxy-3-methylphenyl)propane (Patent Document 1).

Known examples of methods of producing bisphenols include a production method using hydrogen chloride gas as a catalyst (Patent Document 2), a production method using hydrochloric acid as a catalyst (Patent Document 1), a production method using a mixture of hydrochloric acid and sulfuric acid as a catalyst (Patent Document 3), and a production method using sulfuric acid as a catalyst (Patent Document 4).

PRIOR ART DOCUMENTS

Patent Documents

[Patent Document 1] JP 2008-214248 A
[Patent Document 2] JP 62-138443 A
[Patent Document 3] JP 2014-40376 A
[Patent Document 4] JP 2015-51935 A

SUMMARY OF THE INVENTION

Problems to be Solved by the Invention

However, when the present inventors produced 2,2-bis(4-hydroxy-3-methylphenyl)propane by the method described in Patent Document 1, and then used the resulting 2,2-bis(4-hydroxy-3-methylphenyl)propane to produce a polycarbonate resin by melt polymerization reaction, the melt polymerization reaction did not proceed in the expected manner. It was also found that, for production of the polycarbonate resin, the amount of the catalyst in the melt polymerization reaction needs to be increased. Further, the increase in the amount of the catalyst for allowing the melt polymerization reaction to proceed varied depending on the production lot of the 2,2-bis(4-hydroxy-3-methylphenyl)propane, and it was therefore difficult to produce the polycarbonate resin of interest by stably performing the melt polymerization reaction.

A first object of the present invention was carried out in view of such circumstances, aiming to provide a bisphenol composition containing a specific amount of aromatic alcohol sulfonate and a simple method of producing it. The object also aims to provide a method of producing a polycarbonate resin in which, by using the bisphenol composition containing a specific amount of aromatic alcohol sulfonate, melt polymerization reaction can be efficiently allowed to proceed to produce a polycarbonate resin. The object also aims to provide a polycarbonate resin containing an aromatic alcohol sulfonate.

Although the production method using hydrogen chloride gas as a catalyst (Patent Document 2) is known to be a versatile production method for bisphenol, the method requires dedicated equipment when it is industrially carried out since hydrogen chloride gas is highly corrosive. In the production method using hydrochloric acid as a catalyst (Patent Document 1), the amount of hydrogen chloride used is smaller than that in the production method using hydrogen chloride gas as a catalyst. However, concentrated hydrochloric acid is corrosive, and therefore cannot be easily handled. This method also has a problem in that a long reaction time is required. The production method using a mixture of hydrochloric acid and sulfuric acid as a catalyst (Patent Document 3) has a problem of corrosiveness due to the use of hydrochloric acid. In the production method using sulfuric acid as a catalyst (Patent Document 4), side reactions such as sulfonation of phenol easily occur. Therefore, various solvents need to be used in relatively large amounts in order to inhibit the side reactions (Non-patent Document 1). Further, it is known that, since it's necessary to use sulfuric acid in this method, side reactions such as condensation (multimerization) of raw material ketones and aldehydes occur, resulting in the generation of coloring components. Further, as a result of study by the present inventors, it was found that there was a problem that as a result of the solidification of the bisphenol reaction liquid, a long reaction time is needed.

A second object of the present invention was carried out in view of such circumstances, aiming to provide a method of producing a bisphenol which does not cause deterioration of the color tone even in cases of use as a resin material or a developer, producing only a small amount of by-products, while being simple, efficient, and industrially advantageous.

Means for Solving the Problems

In order to achieve the first object, the present inventors studied intensively to discover that a polycarbonate resin can be efficiently produced by using a bisphenol composition containing a specific amount of aromatic alcohol sulfonate, thereby completing the present invention.

More specifically, regarding the first object, the invention can be summarized as the following [1] to [9].

[1] A bisphenol composition comprising an aromatic alcohol sulfonate at not less than 0.1 ppb by mass with respect to a bisphenol.
[2] The bisphenol composition according to [1], wherein, when a mixture of the bisphenol composition and diphenyl carbonate having a ratio of amounts of the diphenyl carbonate to the bisphenol of 1.1 is heated for 90 minutes on an aluminum block heater heated at 194° C., the phenol production rate in a reaction liquid obtained thereafter is not less than 0.3% by area.
[3] The bisphenol composition according to [1] or [2], wherein the aromatic alcohol sulfonate contains a compound represented by General Formula (1) and/or General Formula (2):

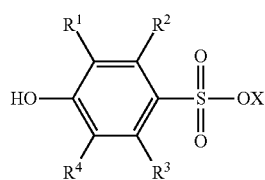

(1)

(wherein $R^1$ to $R^4$ each independently represent a hydrogen atom, halogen atom, alkyl group, alkoxy group, or aryl group; and X represents a hydrogen atom or a metal atom);

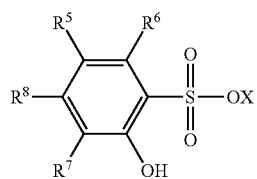

(2)

(wherein $R^5$ to $R^8$ each independently represent a hydrogen atom, halogen atom, alkyl group, alkoxy group, or aryl group; and X represents a hydrogen atom or a metal atom).
[4] The bisphenol composition according to [3], wherein X in the General Formula (1) and/or the General Formula (2) represents a sodium atom or a potassium atom.
[5] The bisphenol composition according to any one of [1] to [4], wherein the content of the aromatic alcohol sulfonate with respect to the bisphenol is not more than 1.0% by mass.
[6] The bisphenol composition according to any one of [1] to [5], wherein the content of the bisphenol in the composition is not less than 95.0% by mass.
[7] A method of producing a bisphenol composition, comprising reacting a ketone or an aldehyde with an aromatic alcohol in the presence of sulfuric acid to produce the bisphenol composition according to any one of [1] to [6].
[8] A method of producing a polycarbonate resin, comprising reacting the bisphenol composition according to any one of [1] to [6] to produce a polycarbonate resin.
[9] A polycarbonate resin comprising an aromatic alcohol sulfonate at not less than 1 ppb by mass in a resin.

In order to achieve the second object, the present inventors studied intensively to discover a method of producing a bisphenol using, as a catalyst, a monoalkyl sulfate obtained by mixing sulfuric acid with an aliphatic alcohol, thereby completing an invention of a method of producing a bisphenol which is simple, efficient, and industrially advantageous.

More specifically, the invention can be summarized as the following [10] to [16].
[10] A method of producing a bisphenol, comprising a step of producing a bisphenol from reaction of an aromatic alcohol with a ketone or an aldehyde, wherein a reaction liquid used for the reaction contains an organic phase and an aqueous phase separated from each other, the aqueous phase containing a monoalkyl sulfate.
[11] The method of producing a bisphenol according to [10], wherein the monoalkyl sulfate is produced from reaction of sulfuric acid with an aliphatic alcohol.
[12] The method of producing a bisphenol according to [11], wherein the sulfuric acid and the aliphatic alcohol are mixed together to produce the monoalkyl sulfate, and then the monoalkyl sulfate is mixed with a reaction liquid containing an aromatic alcohol.
[13] The method of producing a bisphenol according to any one of [10] to [12], wherein the monoalkyl sulfate concentration in the aqueous phase is 0.0001% by mass to 50% by mass.
[14] The method of producing a bisphenol according to any one of [10] to [13], wherein the step of producing a bisphenol is carried out in the presence of a thiol.
[15] The method of producing a bisphenol according to [14], wherein the thiol is mixed with the ketone or the aldehyde, followed by mixing with the monoalkyl sulfate.
[16] A method of producing a polycarbonate resin, comprising producing a bisphenol by the method of producing a bisphenol according to any one of [10] to [15], and then reacting the resulting bisphenol to produce a polycarbonate resin.

Effect of the Invention

According to one embodiment of the present invention, a bisphenol composition containing a specific amount of aromatic alcohol sulfonate, and a simple method of producing it are provided.

More specifically, the present invention can provide a bisphenol composition containing a specific amount of aromatic alcohol sulfonate, which allows melt polymerization reaction to proceed efficiently in production of a polycarbonate resin from a bisphenol, and also allows production of a polycarbonate resin having an excellent color tone.

The present invention also provides a method of producing the bisphenol composition, wherein use of a composition for bisphenol crystallization containing a specific amount of aromatic alcohol sulfonate allows shortening of the time of disappearance of bubbles on the oil-water interface during washing, and allows simple and productive preparation of a bisphenol composition containing an appropriate amount of aromatic alcohol sulfonate.

The present invention can also provide a method of producing a polycarbonate resin by efficient melt polymerization reaction, which method produces a polycarbonate resin having an excellent color tone; and a polycarbonate having an excellent color tone.

According to another mode of the present invention, by using a monoalkyl sulfate as a catalyst, the acid strength of the catalyst can be controlled, and condensation (multimerization) and coloring of raw material ketones and aldehydes can be suppressed, thereby enabling simple and efficient production of a bisphenol with a high yield while production of side reaction products and coloring of the resulting product are reduced. Further, a polymer material such as polycarbonate with reduced coloring can be produced using the bisphenol.

Thus, according to the present invention, simple, efficient, and industrially advantageous methods of producing a variety of bisphenols can be provided. Further, by using bisphenols produced by the production method of the present invention as raw materials of polymer materials such as polycarbonate resins, epoxy resins, and aromatic polyester resins, these resins can be efficiently produced, and moreover, polymer materials such as polycarbonate resins having excellent physical properties can be produced while deterioration of the color tone due to coloring can be suppressed.

MODE FOR CARRYING OUT THE INVENTION

Embodiments of the present invention are described below in detail, but the descriptions of the constituents described below are merely examples of embodiments of the present invention, and the present invention is not limited to the following descriptions as long as the spirit of the present invention is not spoiled.

In the present description, when the term "to" is used with values or physical property values before and after it, it is meant to include those values.

[Bisphenol Composition]

The bisphenol composition as one embodiment of the present invention contains an aromatic alcohol sulfonate at not less than 0.1 ppb by mass with respect to a bisphenol.

Such a bisphenol composition is suitable as a raw material of a polymer such as a polycarbonate resin, and effective for production of the polymer by allowing polymerization reaction efficiently.

Since the bisphenol composition contains a bisphenol, and an aromatic alcohol sulfonate at not less than 0.1 ppb by mass with respect to the bisphenol, the composition may be simply referred to as "bisphenol composition", or alternatively may be referred to as "bisphenol composition containing an aromatic alcohol sulfonate".

Each component of the bisphenol composition is described below.

<Aromatic Alcohol Sulfonate>

"Aromatic alcohol sulfonate" is a salt of an aromatic alcohol sulfonic acid, and examples thereof include sodium salt, potassium salt, lithium salt or the like of an aromatic alcohol sulfonic acid.

"Aromatic alcohol sulfonic acid" is a compound in which one hydrogen atom of an aromatic hydrocarbon is substituted with a hydroxyl group (OH group), and one of the other hydrogen atoms on an aromatic ring, is substituted with a sulfonate group ($SO_2OH$ group).

The aromatic alcohol sulfonic acid may have a structure containing a substituent (that is, a structure containing a substituent other than the OH group and the $SO_2OH$ group), or may have an unsubstituted structure.

The aromatic hydrocarbon as the main backbone of the aromatic alcohol sulfonate may be either monocyclic (a benzene ring) or polycyclic (for example, a naphthalene ring or an anthracene ring).

The aromatic alcohol sulfonate is preferably a hydroxybenzenesulfonic acid. The hydroxybenzenesulfonic acid may contain a substituent.

In particular, 4-hydroxybenzenesulfonate and/or 2-hydroxybenzenesulfonate which may contain a substituent is/are more preferred. More specifically, the aromatic alcohol sulfonate is more preferably a compound(s) represented by the following General Formula (1) and/or General Formula (2).

The following General Formula (1) and General Formula (2) are described below.

Examples of the 4-hydroxybenzenesulfonate include 4-hydroxybenzenesulfonate which may contain a substituent, represented by the following General Formula (1).

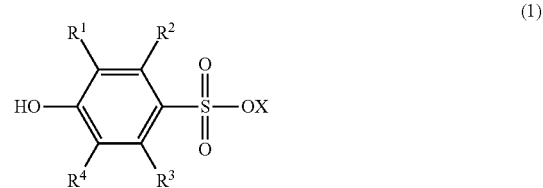

In General Formula (1), each of $R^1$ to $R^4$ is independently a hydrogen atom, a halogen atom, alkyl, alkoxy, aryl, or the like. The alkyl, alkoxy, aryl, or the like may be either substituted or unsubstituted. Their examples include a hydrogen atom; halogen atoms such as fluoro, chloro, bromo, and iodo; $C_1$-$C_{12}$ linear or branched alkyl groups such as methyl, ethyl, n-propyl, propyl, n-butyl, i-butyl, t-butyl, n-pentyl, i-pentyl, n-hexyl, n-heptyl, n-octyl, n-nonyl, n-decyl, n-undecyl, and n-dodecyl; $C_3$-$C_{12}$ cyclic alkyl groups such as cyclopropyl, cyclobutyl, cyclopentyl, cyclohexyl, cycloheptyl, cyclooctyl, and cyclododecyl; $C_1$-$C_{12}$ linear or branched alkoxy groups such as methoxy, ethoxy, n-propoxy, i-propoxy, n-butoxy, i-butoxy, t-butoxy, n-pentyloxy, i-pentyloxy, n-hexyloxy, n-heptyloxy, n-octyloxy, n-nonyloxy, n-decyloxy, n-undecyloxy, and n-dodecyloxy; alkyl groups containing an aryl group as a substituent, such as benzyl; and aryl groups which may contain an alkyl group as a substituent, such as phenyl, tolyl, and xylyl.

Among these, in cases of by-production in the reaction system during the later-mentioned production of a bisphenol, those having a large number of carbons in $R^1$ to $R^4$ tend to cause an increase in the lipophilicity of the hydroxybenzenesulfonate, a decrease in the effect of the surfactant, an increase in the amount of the residual benzenesulfonate with respect to the bisphenol, and deterioration of the color tone of the polycarbonate. In cases where the number of carbons in $R^1$ to $R^4$ is small, the amount of the residual benzenesulfonate with respect to the bisphenol can be controlled to a low level, and the polymerization stability of the polycarbonate can be improved. Thus, a hydrogen atom or $C_1$-$C_2$ alkyl is preferred.

In General Formula (1), specific examples aryl groups which are 4-hydroxyphenyl having $R^1$ to $R^4$ include, but are not limited to, 4-hydroxyphenyl group (wherein $R^1$ to $R^4$ are hydrogen atoms), 4-hydroxytolyl group (wherein, for example, $R^1$ is methyl, and $R^2$ to $R^4$ are hydrogen atoms), and 4-hydroxyxylyl group (wherein, for example, $R^1$ and $R^4$ are methyl, and $R^2$ and $R^3$ are hydrogen atoms).

In General Formula (1), X is a hydrogen atom or a metal atom. Examples of the metal atom include group 1 elements of the periodic table, such as a lithium atom, sodium atom, potassium atom, and cesium atom. Among these, a sodium atom or a potassium atom is preferred, and a sodium atom is more preferred, for they are industrially available at low cost. However, the metal atom is not limited thereto.

Examples of the 2-hydroxybenzenesulfonate include 2-hydroxybenzenesulfonate which may contain a substituent, represented by the following General Formula (2).

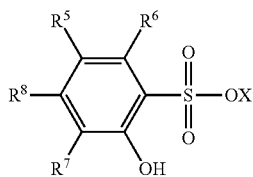
(2)

In General Formula (2), each of $R^5$ to $R^8$ is independently a hydrogen atom, a halogen atom, alkyl, alkoxy, aryl, or the like. The alkyl, alkoxy, aryl, or the like may be either substituted or unsubstituted. Their examples include a hydrogen atom; halogen atoms such as fluoro, chloro, bromo, and iodo; $C_1$-$C_{12}$ linear or branched alkyl groups such as methyl, ethyl, n-propyl, propyl, n-butyl, i-butyl, t-butyl, n-pentyl, i-pentyl, n-hexyl, n-heptyl, n-octyl, n-nonyl, n-decyl, n-undecyl, and n-dodecyl; $C_3$-$C_{12}$ cyclic alkyl groups such as cyclopropyl, cyclobutyl, cyclopentyl, cyclohexyl, cycloheptyl, cyclooctyl, and cyclododecyl; $C_1$-$C_{12}$ linear or branched alkoxy groups such as methoxy, ethoxy, n-propoxy, i-propoxy, n-butoxy, i-butoxy, t-butoxy, n-pentyloxy, i-pentyloxy, n-hexyloxy, n-heptyloxy, n-octyloxy, n-nonyloxy, n-decyloxy, n-undecyloxy, and n-dodecyloxy; alkyl groups containing an aryl group as a substituent, such as benzyl; and aryl groups which may contain an alkyl group as a substituent, such as phenyl, tolyl, and xylyl.

Among these, in cases of by-production in the reaction system during the later-mentioned production of a bisphenol, those having a large number of carbons in $R^5$ to $R^8$ tend to cause an increase in the lipophilicity of the hydroxybenzenesulfonate, a decrease in the effect of the surfactant, an increase in the amount of the residual benzenesulfonate with respect to the bisphenol, and deterioration of the color tone of the polycarbonate. In cases where the number of carbons in $R^5$ to $R^8$ is small, the amount of the residual benzenesulfonate with respect to the bisphenol can be controlled to a low level, and the polymerization stability of the polycarbonate can be improved. Thus, a hydrogen atom or $C_1$-$C_2$ alkyl is preferred.

In General Formula (2), specific examples of aryl groups which are 2-hydroxyphenyl having $R^5$ to $R^8$ include, but are not limited to, 2-hydroxyphenyl (wherein $R^5$ to $R^8$ are hydrogen atoms), 2-hydroxytolyl (wherein, for example, $R^7$ is methyl, and $R^5$, $R^6$, and $R^8$ are hydrogen atoms).

In General Formula (2), X is a hydrogen atom or a metal atom. Examples of the metal atom include group 1 elements of the periodic table, such as a lithium atom, sodium atom, potassium atom, and cesium atom. Among these, a sodium atom or a potassium atom is preferred, and a sodium atom is more preferred, for they are industrially available at low cost. However, the metal atom is not limited thereto.

Specific examples of the hydroxybenzenesulfonate represented by General Formula (1) or General Formula (2) include, but are not limited to, sodium 4-hydroxybenzenesulfonate, sodium 2-hydroxybenzenesulfonate, sodium 4-hydroxy-3-methylbenzenesulfonate, sodium 2-hydroxy-3-methylbenzenesulfonate, and sodium 4-hydroxy-3,5-dimethylbenzenesulfonate.

Among these, sodium 4-hydroxy-3-methylbenzenesulfonate and sodium 2-hydroxy-3-methylbenzenesulfonate are preferred since, in the later-mentioned production of a bisphenol, these can be included in the resulting bisphenol product as by-product in the reaction system.

The bisphenol composition may contain only one kind of aromatic alcohol sulfonate, or may contain two or more kinds of aromatic alcohol sulfonate.

For example, the bisphenol composition, which contains a predetermined amount of aromatic alcohol sulfonate, may be a bisphenol composition containing 4-hydroxybenzenesulfonate and 2-hydroxybenzenesulfonate in a total amount of 1 ppb by mass to 100 ppm by mass with respect to bisphenol.

In general, in a composition that has not been particularly treated, sodium element is detected in several tens of ppb order. Whether the sodium element forms a salt with sulfonic acid or not can be clearly judged based on whether reaction with diphenyl carbonate occurs or not. That is, in cases where sulfonate is present, the reaction with diphenyl carbonate proceeds to produce bisphenol, while in cases where sulfonate is absent, no bisphenol is produced.

In the present invention, production of the sulfonate required for the present invention can be confirmed based on the fact that, when a mixture of the bisphenol and the diphenyl carbonate having a ratio of amounts of the diphenyl carbonate to the bisphenol composition of 1.1 is heated for 90 minutes on an aluminum block heater heated at 194° C., the phenol production rate in a reaction liquid obtained thereafter is not less than 0.3% by area.

<Bisphenol>

The bisphenol contained in the bisphenol composition is usually a compound represented by the following General Formula (3).

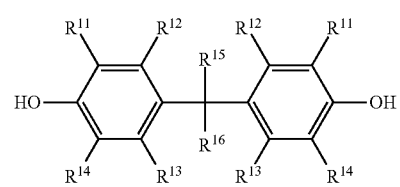
(3)

In the General Formula (3), $R^{11}$, $R^{12}$, $R^{13}$, and $R^{14}$ may be either the same or different. Each of the two of $R^{11}$, $R^{12}$, $R^{13}$, or $R^{14}$ present in General Formula (3) may be different from each other, but, from the viewpoint of convenience during the synthesis and availability, each of the two of $R^{11}$, $R^{12}$, $R^{13}$, or $R^{14}$ are preferably the same. Examples, and preferred examples, of $R^{11}$ to $R^{14}$ include those exemplified as $R^1$ to $R^4$ in General Formula (1) and $R^5$ to $R^8$ in General Formula (2) (wherein $R^1$ and $R^7$ correspond to $R^{11}$; $R^2$ and $R^8$ correspond to $R^{19}$; $R^3$ and $R^6$ correspond to $R^{13}$; and $R^4$ corresponds to $R^{14}$).

Each of $R^{15}$ and $R^{16}$ is independently a hydrogen atom, alkyl, alkoxy, aryl, or the like. The alkyl, alkoxy, aryl, or the like may be either substituted or unsubstituted. Their examples include a hydrogen atom; $C_1$-$C_{20}$ linear or branched alkyl groups such as methyl, ethyl, n-propyl, i-propyl, n-butyl, i-butyl, t-butyl, n-pentyl, i-pentyl, n-hexyl, n-heptyl, n-octyl, 2-ethylhexyl, n-nonyl, n-decyl, n-undecyl, and n-dodecyl; $C_3$-$C_{20}$ cyclic alkyl groups such as cyclopropyl, cyclobutyl, cyclopentyl, cyclohexyl, cycloheptyl, cyclooctyl, and cyclododecyl; $C_1$-$C_{20}$ linear or branched alkoxy groups such as methoxy, ethoxy, n-propoxy, propoxy, n-butoxy, i-butoxy, t-butoxy, n-pentyloxy, pentyloxy, n-hexyloxy, n-heptyloxy, n-octyloxy, n-nonyloxy, n-decyloxy, n-undecyloxy, and n-dodecyloxy; alkyl groups containing an aryl group as a substituent, such as benzyl; and aryl groups which may contain an alkyl group as a substituent, such as phenyl, tolyl, and 2,6-dimethylphenyl.

In General Formula (3), $R^{15}$ and $R^{16}$ may be bound or cross-linked to each other. Examples of such $R^{15}$ and $R^{16}$ include linking groups such as cyclopropylidene, cyclobutylidene, cyclopentylidene, cyclohexylidene, 3,3,5-trimethylcyclohexylidene, cycloheptylidene, cyclooctylidene, cyclononylidene, cyclodecylidene, cycloundecylidene, cyclododecylidene, fluorenylidene, xanthonilydene, thioxanthonylidene and the like.

Examples of the bisphenol contained in the bisphenol composition include, but are not limited to, 2,2-bis(4-hydroxyphenyl)propane, 2,2-bis(4-hydroxy-3-methylphenyl)propane, 1,1-bis(4-hydroxy-3-methylphenyl)cyclohexane, 9,9-bis(4-hydroxy-3-methylphenyl)fluorene, 3,3-bis(4-hydroxyphenyl)pentane, 3,3-bis(4-hydroxy-3-methylphenyl)pentane, 2,2-bis(4-hydroxyphenyl)pentane, 2,2-bis(4-hydroxy-3-methylphenyl)pentane, 3,3-bis(4-hydroxyphenyl)heptane, 3,3-bis(4-hydroxy-3-methylphenyl)heptane, 2,2-bis(4-hydroxyphenyl)heptane, 2,2-bis(4-hydroxy-3-methylphenyl)heptane, 4,4-bis(4-hydroxyphenyl)heptane, and 4,4-bis(4-hydroxy-3-methylphenyl)heptane.

Among these, a preferred example of the bisphenol is 2,2-bis(4-hydroxy-3-methylphenyl)propane.

For allowing the aromatic alcohol sulfonate contained in the bisphenol composition to sufficiently produce an effect as a polymerization catalyst during production of a polymer such as a polycarbonate resin, the content of the aromatic alcohol sulfonate with respect to the bisphenol is not less than 0.1 ppb by mass, preferably not less than 1 ppb by mass, more preferably not less than 5 ppb by mass, still more preferably not less than 8 ppb by mass, especially preferably not less than 10 ppb by mass.

On the other hand, in cases where the content of the aromatic alcohol sulfonate is too high with respect to the bisphenol, the color tone of the polycarbonate using the bisphenol composition is deteriorated. The content is therefore usually not more than 1.0% by mass, preferably not more than 100 ppm by mass, more preferably not more than 80 ppm by mass, still more preferably not more than 50 ppm by mass.

The bisphenol composition contains a bisphenol as a major component, and the bisphenol is usually contained at not less than 95.0% by mass in the bisphenol composition. The content of the bisphenol in the bisphenol composition is preferably not less than 97.0% by mass, more preferably not less than 98.0% by mass, still more preferably not less than 98.5% by mass, most preferably not less than 99.0% by mass.

The content of components besides the bisphenol and the aromatic alcohol sulfonate in the bisphenol composition is preferably low.

In particular, for the use of a raw material of a polycarbonate resin, the content of components that inhibit polymerization with diester carbonate is preferably low in the bisphenol composition.

In a later-mentioned method of producing a bisphenol composition (Method 4), components that inhibit polymerization with diester carbonate can be efficiently removed to produce a bisphenol composition in which the content of the components that inhibit polymerization with diester carbonate is extremely low. Thus, a bisphenol composition obtained by the method of producing a bisphenol composition (Method 4) can be suitably used as a raw material of a polycarbonate resin.

[Method of Producing Bisphenol Composition]

The method of producing a bisphenol composition is not limited, and examples of the method include the following.

(Method 1) A method in which a solid bisphenol is mixed with an aromatic alcohol sulfonate whose content is not less than 0.1 ppb by mass with respect to the bisphenol, to obtain a bisphenol composition.

(Method 2) A method in which a molten bisphenol is mixed with an aromatic alcohol sulfonate whose content is not less than 0.1 ppb by mass with respect to the bisphenol, to obtain a bisphenol composition.

(Method 3) A method in which an aromatic alcohol sulfonate is produced as a by-product during production of a bisphenol, and then purification is carried out when necessary, to obtain a bisphenol composition.

(Method 4) A method in which a composition for bisphenol crystallization containing an aromatic alcohol sulfonate at more than 100 ppm by mass and not more than 1% by mass with respect to a bisphenol is dissolved in a solvent to provide a solution, and the solution is washed with water, followed by subjecting the resulting organic phase to crystallization to obtain a bisphenol composition.

In the methods of (Method 1) and (Method 2), in which an aromatic alcohol sulfonate is mixed with a solid or molten bisphenol, the quality of the solid or molten bisphenol in use influences the quality of the bisphenol composition. Therefore, the quality of the resulting bisphenol composition tends to be uneven. Further, the aromatic alcohol sulfonate needs to be provided separately.

From these reasons, (Method 3) the method in which an aromatic alcohol sulfonate is produced as a by-product in a reaction system for production of a bisphenol, to include a hydroxybenzenesulfonate in the bisphenol composition; and (Method 4) the method in which a composition for bisphenol crystallization is subjected to crystallization to obtain a bisphenol composition; are preferred.

The (Method 3) and the (Method 4) are described below in detail.

<Production Method of (Method 3)>

Examples of the method in which an aromatic alcohol sulfonate is produced as a by-product together with a bisphenol in the reaction system during production of the bisphenol to obtain a bisphenol composition include a method in which a ketone or an aldehyde is condensed with an aromatic alcohol in the presence of sulfuric acid, which is an acid catalyst, to produce a bisphenol. By this method, an aromatic alcohol sulfonate derived from the aromatic alcohol can be produced in the reaction system.

In cases where the amount of the aromatic alcohol sulfonate produced as a by-product in the bisphenol reaction system is too large, purification may be carried out such that the aromatic alcohol sulfonate is contained within a range specified for the bisphenol composition. For example, the resulting bisphenol product may be further subjected to washing with water, crystallization, suspension washing, and sprinkle-washing, to remove part of the aromatic alcohol sulfonate contained in the bisphenol product, thereby controlling the bisphenol composition such that the aromatic alcohol sulfonate is contained within the specified range. Details of the process are described later.

As a method in which a bisphenol is produced utilizing reaction of a ketone or an aldehyde with an aromatic alcohol, a method of producing a bisphenol as one embodiment of the present invention may be employed. This is a method of producing bisphenol, comprising the step of producing a bisphenol by the reaction of an aromatic alcohol with a ketone or an aldehyde, wherein a reaction liquid used for the reaction contains an organic phase and an aqueous phase separated from each other, the aqueous phase containing a monoalkyl sulfate.

The bisphenol obtained by the production method according to the embodiment is highly pure, and hardly shows coloring. Therefore, the bisphenol can be used in a method of producing a highly pure polycarbonate. For example, a highly pure polycarbonate can be obtained by carrying out polycondensation of a bisphenol obtained by the production method of the present invention with diphenyl carbonate in the presence of a transesterification catalyst.

In the production of a bisphenol, the bisphenol is preferably produced by condensing an aromatic alcohol with a ketone or an aldehyde using sulfuric acid as a catalyst, and also using an aliphatic alcohol.

The bisphenol production reaction is carried out, for example, according to the following Reaction Formula (4). In this reaction, by using, for example, sulfuric acid as a catalyst, a hydroxybenzenesulfonate represented by the following General Formula (e) (1A) and/or (2A) corresponding to the raw material aromatic alcohol can be produced as by-product.

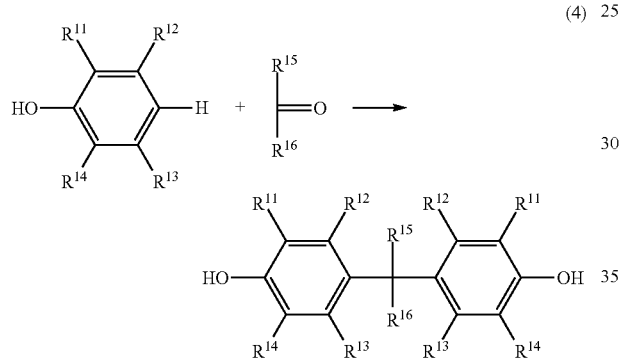

(4)

(In the formula, $R^{11}$ to $R^{16}$ have the same meanings as in General Formula (3). $R^{12}$ and $R^{13}$ are preferably protons since the condensation reaction hardly proceeds in cases where they are sterically bulky.)

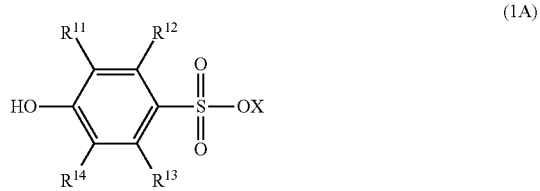

(1A)

(In the formula, $R^{11}$ to $R^{14}$ have the same meanings as in General Formula (3).)

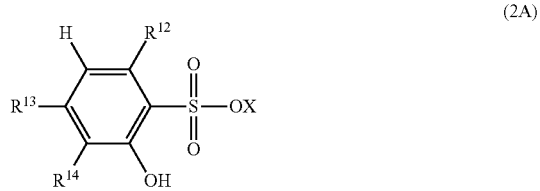

(2A)

(In the formula, $R^{12}$ to $R^{14}$ have the same meanings as in General Formula (3).)

(Aromatic Alcohol)

The aromatic alcohol used as a raw material of the bisphenol is usually a compound represented by the following General Formula (5).

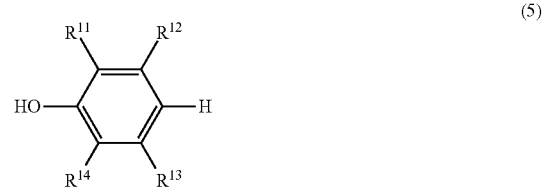

(5)

(In the formula, $R^{11}$ to $R^{14}$ have the same meanings as in General Formula (3). $R^{12}$ and $R^{13}$ are preferably protons since the condensation reaction hardly proceeds in cases where they are sterically bulky.)

Specific examples of the compound represented by the General Formula (5) include phenol, methylphenol, dimethylphenol, ethylphenol, propylphenol, butylphenol, methoxyphenol, ethoxyphenol, propoxyphenol, butoxyphenol, aminophenol, benzylphenol, and phenylphenol.

(Ketone or Aldehyde)

The ketone or the aldehyde is usually a compound represented by the following General Formula (6).

(6)

(In the formula, $R^{15}$ and $R^{16}$ have the same meanings as in General Formula (3).)

Specific examples of the compound represented by General Formula (6) include aldehydes such as formaldehyde, acetaldehyde, propionaldehyde, butylaldehyde, pentanaldehyde, hexanaldehyde, heptanaldehyde, octanaldehyde, nonanaldehyde, decanaldehyde, undecanaldehyde, and dodecanaldehyde; ketones such as acetone, butanone, pentanone, hexanone, heptanone, octanone, nonanone, decanone, undecanone, and dodecanone; aryl alkyl ketones such as benzaldehyde, phenyl methyl ketone, phenyl ethyl ketone, phenyl propyl ketone, cresyl methyl ketone, cresyl ethyl ketone, cresyl propyl ketone, xylyl methyl ketone, xylyl ethyl ketone, and xylyl propyl ketone; and cyclic alkane ketones such as cyclopropanone, cyclobutanone, cyclopentanone, cyclohexanone, cycloheptanone, cyclooctanone, cyclononanone, cyclodecanone, cycloundecanone, and cyclododecanone.

In the reaction of condensing the aromatic alcohol with the ketone or the aldehyde, in cases where the molar ratio of the aromatic alcohol to the ketone or the aldehyde ((the number of moles of the aromatic alcohol/the number of moles of the ketone) or (the number of moles of the aromatic alcohol/the number of moles of the aldehyde)) is low, the ketone or the aldehyde is prone to multimerize, while in cases where the ratio is high, the aromatic alcohol is lost while remaining unreacted. From these reasons, the molar ratio of the aromatic alcohol to the ketone or the aldehyde is preferably not less than 1.5, more preferably not less than 1.6, still more preferably a molar ratio of not less than 1.7, and is preferably not more than 15, more preferably not more than 10, still more preferably not more than 8.

Usually, in the reaction of condensing the aromatic alcohol with the ketone or the aldehyde, the ketone or the aldehyde is fed to a mixed solution of the aromatic alcohol and the acid catalyst. This method of feeding the ketone or the aldehyde may be a method in which the ketone or the aldehyde is fed at once, or may be a method in which the ketone or the aldehyde is fed dividedly. Since the reaction for producing the bisphenol is an exothermic one, the method is preferably a method in which the ketone or the aldehyde is fed dividedly by, for example, slowly feeding in a dropwise manner.

(Sulfuric Acid)

The sulfuric acid that can be used as a catalyst can be fed into the reaction system by using an aqueous sulfuric acid solution (raw material sulfuric acid) prepared by dilution of sulfuric acid with water, which is called concentrated sulfuric acid or dilute sulfuric acid. As the raw material sulfuric acid, either concentrated sulfuric acid or dilute sulfuric acid may be used. However, in cases where the concentration of the raw material sulfuric acid is too high, multimerization of the ketone or the aldehyde may be promoted, or sulfonation of the produced bisphenol may occur. Further in cases where the later-mentioned aliphatic alcohol or thiol is used in combination, dehydration dimerization of the aliphatic alcohol may be promoted, or degradation of the thiol may occur. On the other hand, in cases where the concentration of the raw material sulfuric acid used is too low, the reaction time increases, and therefore the bisphenol cannot be produced efficiently. Thus, the mass concentration of the raw material sulfuric acid is preferably not less than 50% by mass, more preferably not less than 60% by mass. Further, in a case where the sulfuric acid concentration is high (that is, where the concentration of water in the sulfuric acid is low), and, at the same time, where the amount of the solvent preliminarily mixed with acetone (see later-mentioned details) with respect to the amount of water contained in the sulfuric acid is small, the acetone may be multimerized into mesityl oxide (a dimer product) and the like, promoting dehydration dimerization of the aliphatic alcohol and causing oxidative degradation of the thiol. Thus, the mass concentration of the raw material sulfuric acid used is preferably not more than 95% by mass, more preferably not more than 90% by mass. On the other hand, in a case where the sulfuric acid concentration is high (that is, where the concentration of water in the sulfuric acid is low), and, at the same time, where the amount of the solvent preliminarily mixed with acetone (see later-mentioned details) with respect to the amount of water contained in the sulfuric acid is large, the acetone is capable of suppressing multimerization of mesityl oxide (a dimer product) and the like, suppressing dehydration dimerization of the aliphatic alcohol, and suppressing oxidative degradation of the thiol. Thus, the concentration of the sulfuric acid used is preferably not less than 90% by weight, more preferably not less than 95% by weight.

In cases where the molar ratio of the sulfuric acid to the ketone or the aldehyde ((the number of moles of the sulfuric acid/the number of moles of the ketone) or (the number of moles of the sulfuric acid/the number of moles of the aldehyde)) is low, dilution of the sulfuric acid occurs with by-product water from the condensation reaction, leading to requirement of a long reaction time. On the other hand, in cases where the molar ratio is high, multimerization of the ketone or the aldehyde may proceed. From these reasons, the molar ratio of the sulfuric acid to the ketone or the aldehyde is preferably not less than 0.0001, more preferably not less than 0.01, still more preferably not less than 0.05, especially preferably not less than 0.1, and is preferably not more than 10, more preferably not more than 8, still more preferably not more than 5, especially preferably not more than 3.

(Reaction Liquid)

The reaction liquid used for the reaction of the aromatic alcohol with the ketone or the aldehyde contains an organic phase and an aqueous phase separated from each other, and the aqueous phase contains a monoalkyl sulfate. The aromatic alcohol is contained in the organic phase, and the ketone or the aldehyde is separated into the organic phase.

By the inclusion of the monoalkyl sulfate, the acid strength of the catalyst can be controlled, and condensation (multimerization) and coloring of the raw material ketone or aldehyde can be suppressed. Thus, excessive production of the aromatic alcohol sulfonate can be suppressed, and a bisphenol can be simply and efficiently produced with a reduced coloring of the product. In addition, with the residual content of the aliphatic alcohol used for the generation of the monoalkyl sulfate, the produced bisphenol can be dissolved to suppress solidification of the reaction liquid, and the mixed state is improved, thereby enabling shortening of the reaction time, which is advantageous.

(Monoalkyl Sulfate)

Examples of the monoalkyl sulfate include monomethyl sulfate, monoethyl sulfate, monopropyl sulfate, monoisopropyl sulfate, monobutyl sulfate, monoisobutyl sulfate, mono t-butyl sulfate, monopentyl sulfate, monoisopentyl sulfate, monohexyl sulfate, monoheptyl sulfate, monooctyl sulfate, monononyl sulfate, monodecyl sulfate, monoundecyl sulfate, monododecyl sulfate, mono(hydroxyethyl) sulfate, mono(2-hydroxyethoxyethyl) sulfate, and mono(2-(2'-hydroxyethoxy)ethoxyethyl) sulfate. Among these, monoalkyl sulfate having not more than 8 carbon atoms is preferably used since, lipophilicity increases when the number of carbons is large, and therefore transfer of the monoalkyl sulfate between the organic phase and the aqueous phase becomes difficult.

The method of producing the monoalkyl sulfate is not limited, and, from the viewpoint of obtaining the monoalkyl sulfate simply and at low cost, one example that can be named is a method in which the monoalkyl sulfate is produced by reaction between sulfuric acid and an aliphatic alcohol.

The concentration of the monoalkyl sulfate can be determined by, for example, removing part of the aqueous phase obtained after mixing the aliphatic alcohol with sulfuric acid, and then analyzing the aqueous phase by $^1$H NMR. Examples of the aqueous phase obtained after mixing the aliphatic alcohol with sulfuric acid include: (1) an aqueous phase obtained by mixing the aliphatic alcohol with sulfuric acid; (2) an aqueous phase obtained by mixing the aliphatic alcohol, an aromatic alcohol, a solvent, a thiol, and sulfuric acid together, and then leaving the resulting mixture to stand; (3) an aqueous phase obtained by mixing the aliphatic alcohol with an aromatic alcohol, feeding sulfuric acid thereto, and then leaving the resulting mixture to stand; (4) an aqueous phase obtained by mixing the aliphatic alcohol, a solvent, and an aromatic alcohol together, feeding sulfuric acid thereto, mixing the resulting mixture, and then leaving the mixture to stand; and (5) an aqueous phase obtained by leaving a bisphenol reaction liquid to stand. The concentration of the monoalkyl sulfate in the reaction liquid is preferably 0.0001% by weight to 50% by weight.

Examples of the method of preparing the monoalkyl sulfate include a method in which the sulfuric acid shown below is mixed with the aliphatic alcohol shown below to obtain the monoalkyl sulfate, and a method in which a metal salt of a monoalkyl sulfate such as a sodium monoalkyl sulfate is mixed with sulfuric acid to obtain the monoalkyl sulfate. In the present invention, regarding the monoalkyl sulfate that is allowed to be present in the bisphenol production step, it may be preliminarily prepared and then mixed with at least part of the reaction raw material, thereby allowing the presence. Alternatively, the monoalkyl sulfate may be produced by allowing sulfuric acid and an aliphatic alcohol to coexist in the reaction system for the production of the bisphenol, thereby allowing the presence in the reaction system.

Since mixing of the aliphatic alcohol with sulfuric acid generates heat, the mixing is preferably carried out at not more than the boiling point of the aliphatic alcohol.

The reaction of producing the bisphenol from the aromatic alcohol and the ketone or the aldehyde is preferably carried out in a solvent. Thus, examples of the method include a method in which feeding of the monoalkyl sulfate is carried out after feeding the aromatic alcohol, the solvent, the ketone or the aldehyde, and, when necessary, thiol into the reactor, and a method in which, before feeding and mixing of the ketone or the aldehyde in the reactor, the monoalkyl sulfate is fed to the reactor, and the monoalkyl sulfate is mixed with the aromatic alcohol and the like, followed by mixing with the ketone or the aldehyde. From the viewpoint of avoiding multimerization of the ketone or the aldehyde, a method in which, before feeding the ketone or the aldehyde to the reactor, the monoalkyl sulfate is fed to the reactor, and then the ketone or the aldehyde is mixed therewith is preferred.

(Aliphatic Alcohol)

Examples of the aliphatic alcohol include $C_1$-$C_{12}$ alkyl alcohols such as methanol, ethanol, n-propanol, propanol, n-butanol, i-butanol, t-butanol, n-pentanol, pentanol, n-hexanol, n-heptanol, n-octanol, n-nonanol, n-decanol, n-undecanol, n-dodecanol, ethylene glycol, diethylene glycol, and triethylene glycol. As the number of carbon atoms in the aliphatic alcohol increases, lipophilicity increases. In such a case, the aliphatic alcohol can be hardly mixed with sulfuric acid, and therefore the monoalkyl sulfate can be hardly obtained. Thus, the aliphatic alcohol is preferably an alkyl alcohol having not more than 8 carbon atoms, especially preferably methanol.

In cases where the molar ratio of the aliphatic alcohol to the sulfuric acid (the number of moles of the aliphatic alcohol/the number of moles of the sulfuric acid) is low, the amount of the monoalkyl sulfate produced is small, and the reaction takes a long time, while in cases where the molar ratio is high, the sulfuric acid concentration is low. From these reasons, the molar ratio of the aliphatic alcohol to the sulfuric acid is preferably not less than 0.0001, more preferably not less than 0.01, still more preferably not less than 0.05, especially preferably not less than 0.1, and is preferably not more than 10, more preferably not more than 5, still more preferably not more than 3.

(Thiol)

In the reaction of condensing the aromatic alcohol with the ketone or the aldehyde, a thiol may be used as a promoter. Examples of the thiol used as a promoter include mercapto carboxylic acids such as mercapto acetic acid, thioglycolic acid, 2-mercaptopropionic acid, 3-mercaptopropionic acid, and 4-mercaptobutyric acid; methyl mercaptan, ethyl mercaptan, propyl mercaptan, butyl mercaptan, pentyl mercaptan, hexyl mercaptan, heptyl mercaptan, octyl mercaptan, nonyl mercaptan, decyl mercaptan (decanethiol), undecyl mercaptan (undecanethiol), dodecyl mercaptan (dodecanethiol), tridecyl mercaptan, tetradecyl mercaptan, and pentadecyl mercaptan.

In cases where the molar ratio of the thiol to the ketone or the aldehyde ((the number of moles of the thiol/the number of moles of the ketone) or (the number of moles of the thiol/the number of moles of the aldehyde)) is low, the effect for improving the bisphenol selectivity by the use of the thiol promoter cannot be obtained, while in cases where the molar ratio is high, the quality may be deteriorated due to contamination in the bisphenol. From these reasons, the molar ratio of the thiol to the ketone and the aldehyde is preferably not less than 0.001, more preferably not less than 0.005, still more preferably not less than 0.01, and is preferably not more than 1, more preferably not more than 0.5, still more preferably not more than 0.1.

From the viewpoint of preventing oxidative degradation of the thiol, the thiol is preferably preliminarily mixed with the ketone or the aldehyde before being subjected to the reaction. Regarding the method for mixing together the thiol and the ketone or the aldehyde, the ketone or the aldehyde may be mixed into the thiol, or the thiol may be mixed into the ketone or the aldehyde. Regarding the method for mixing together the mixed liquid of the thiol and the ketone or the aldehyde, and the raw material sulfuric acid, the raw material sulfuric acid may be mixed into the mixed liquid, or the mixed liquid may be mixed into the raw material sulfuric acid. Preferably, the mixed liquid is mixed into the raw material sulfuric acid. More preferably, after the raw material sulfuric acid and the aromatic alcohol are fed to the reaction vessel, the mixed liquid is fed to the reaction vessel and mixed.

(Solvent)

As a solvent for the production reaction of the bisphenol composition, an aromatic hydrocarbon may be used. The solvent that has been used for the production of the bisphenol may be recovered by distillation or the like, and then purified for reusing it. Examples of the aromatic hydrocarbon used include benzene, toluene, xylene, ethylbenzene, diethylbenzene, isopropylbenzene, and mesitylene. In cases where the solvent is reused, the solvent is preferably a solvent having a low boiling point.

Alternatively, without using the solvent, a large amount of the raw material aromatic alcohol may be used instead of the solvent. In such cases, loss of unreacted aromatic alcohol occurs. For reducing the loss, it may be recovered by distillation or the like, and then purified for reusing it.

In cases where the amount of the solvent fed to the reaction for producing the bisphenol is too small with respect to, for example, the amount of the sulfuric acid used for the preparation of the monoalkyl sulfate, the produced bisphenol may be degraded, so that the resulting bisphenol may decrease. On the other hand, in cases where the amount of the solvent is too large with respect to the amount of the sulfuric acid, the condensation reaction rate between the ketone or the aldehyde and the aromatic alcohol may be low, so that the production of the bisphenol may take a long time. Thus, the amount of the solvent used is preferably not less than 0.05 times, more preferably not less than 0.1 times, and is preferably not more than 10 times, more preferably not more than 5 times the amount of the sulfuric acid. In particular, in cases where a high concentration of sulfuric acid is used, the amount of the solvent is preferably not less than 1 time, more preferably not less than 2 times, and is preferably not more than 10 times, more preferably not more than 5 times the amount of the sulfuric acid.

Alternatively, without using the solvent, a large amount of aromatic alcohol may be used instead of the solvent. Since loss of unreacted aromatic alcohol occurs, it may be recovered by distillation or the like, and then purified for reusing it.

(Bisphenol Production Reaction)

The bisphenol production reaction is a condensation reaction. In cases where the reaction temperature during the production reaction is too high, oxidative degradation of the promoter is likely to proceed due to the catalyst, while in cases where the reaction temperature is too low, the reaction takes a long time. Thus, the reaction temperature is preferably 0° C. to 50° C.

In cases where the reaction time of the production reaction is too long, degradation of the produced bisphenol may occur. Thus, the reaction time is preferably not more than 30 hours, more preferably not more than 25 hours, still more preferably not more than 20 hours. The reaction time is usually not less than 15 hours. By adding water in an amount equivalent to or larger than the amount of the sulfuric acid to reduce the sulfuric acid concentration, the reaction can be stopped.

(Bisphenol Purification)

The bisphenol obtained by the bisphenol production reaction may be purified by an ordinary method. For example, the bisphenol may be purified by simple means such as crystallization or column chromatography. In one example, after the condensation reaction, an organic phase obtained by separation of the reaction liquid is washed with water, brine, or the like, and then, if necessary, neutralized by washing with aqueous sodium bicarbonate or the like. When necessary, the washed organic phase may be cooled to allow crystallization. In cases where a large amount of aromatic alcohol is used, excessive aromatic alcohol is preferably removed by distillation before the crystallization during the purification.

<Production Method of (Method 4)>

(Method 4) is a method in which a composition for bisphenol crystallization containing an aromatic alcohol sulfonate at more than 100 ppm by mass and not more than 1% by mass with respect to a bisphenol is dissolved in a solvent to provide a solution, and the resulting solution is washed with water, followed by subjecting the resulting organic phase to crystallization to obtain a bisphenol composition.

As described above, the content of melt polymerization reaction-inhibiting components in the bisphenol composition is preferably low. For production of such a bisphenol composition, the production method of (Method 4) is suitable.

The present inventors revealed that components that inhibit the melt polymerization reaction are likely to be contained in the bisphenol. The present inventors then discovered that the components that inhibit the melt polymerization reaction (melt polymerization reaction-inhibiting components) can be easily removed by using a composition for bisphenol crystallization containing an aromatic alcohol sulfonate at more than 100 ppm by mass and not more than 1% by mass with respect to the bisphenol (which may be hereinafter simply referred to as "composition for bisphenol crystallization"), more specifically, by subjecting a solution containing the composition for bisphenol crystallization dissolved therein to washing with water and then to oil-water separation, followed by performing crystallization of the organic phase.

This is predicted to be due to the following reason. Since the composition for bisphenol crystallization containing an aromatic alcohol sulfonate at more than 100 ppm by mass and not more than 1% by mass with respect to the bisphenol is used, the aromatic alcohol sulfonate contained in the composition for bisphenol crystallization acts as a surfactant. Thus, separation into the aqueous phase and the organic phase can be easily achieved during the washing with water, and the residual melt polymerization reaction-inhibiting components can be reduced in the organic phase, in which the bisphenol composition is dissolved. Accordingly, the melt polymerization reaction-inhibiting components can be easily and efficiently removed into the aqueous phase.

Thus, by using the production method of (Method 4), a bisphenol composition, especially a bisphenol composition in which the content of melt polymerization reaction-inhibiting components is small, can be simply and efficiently obtained.

Further, by using a bisphenol composition obtained by the production method of (Method 4), melt polymerization reaction can be stably carried out to enable a stable production of a polycarbonate resin by the melt polymerization reaction.

In cases where the composition for bisphenol crystallization contains the aromatic alcohol sulfonate at more than 1% by mass with respect to the bisphenol, excessive aromatic alcohol sulfonate is likely to remain in the bisphenol composition after crystallization, leading to low reactivity with diester carbonate in some cases. The amount of the aromatic alcohol sulfonate with respect to the bisphenol is usually not more than 1% by mass, preferably not more than 0.5% by mass, more preferably not more than 0.1% by mass.

Further, in cases where the amount of the aromatic alcohol sulfonate with respect to the bisphenol is not more than 100 ppm by mass, its effect as a surfactant is insufficient, so that the organic phase and the aqueous phase can be hardly separated from each other during the oil-water separation. Thus, a large amount of components which inhibit the reaction with the diester carbonate, contained in the bisphenol, are easy to remain in the organic phase. Further, since the separation between the organic phase and the aqueous phase takes a long time, such cases are also not preferred from an economic point of view. The amount of the aromatic alcohol sulfonate contained in the composition for bisphenol crystallization with respect to the bisphenol is usually more than 100 ppm by mass, preferably not less than 150 ppm by mass, more preferably not less than 195 ppm by mass, still more preferably not less than 300 ppm by mass.

In one example of the production method of (Method 4), a bisphenol composition can be produced from a crude product of bisphenol by the following method.

A composition for bisphenol crystallization containing an aromatic alcohol sulfonate at more than 100 ppm by mass and not more than 1% by mass with respect to a bisphenol is mixed with an organic solvent (toluene, xylene, trimethylbenzene, or the like), and the resulting mixture is stirred at 60 to 95° C. to obtain a solution (A) in which the bisphenol and the aromatic alcohol sulfonate are dissolved. Water (demineralized water, ion-exchanged water, or the like) in an amount of 0.1 to 10 parts by mass with respect to 1 part by mass of the solution (A) is added, and the resulting mixture is stirred at 60 to 95° C. for 0.1 to 1 hour. After completion of the stirring, the mixture is left to stand at 60 to 95° C. to allow oil-water separation. After the oil-water separation, the aqueous phase is removed to obtain an organic phase (A). From the organic phase (A), a bisphenol is precipitated. Thereafter, solid-liquid separation and drying are carried out to obtain a bisphenol composition.

Examples of the methods for precipitating the bisphenol from the organic phase (A) include a method in which the temperature is decreased from a temperature of 60 to 95° C. to a temperature of 0 to 20° C. for 1 to 10 hours to allow crystallization. The crystallization time costs about 1 to 10 hours.

The method of the solid-liquid separation of the precipitated bisphenol composition is not limited, and an ordinary method such as filtration, centrifugation, or decantation may be used.

The method of the drying may be either drying under a reduced pressure or drying under a normal pressure. Although the drying temperature may be determined appropriately, it is preferably to be 50 to 120° C. from the viewpoint that, in cases where the drying temperature is high, fusion of the bisphenol composition occurs to prevent the removal of the composition from the apparatus.

The composition for bisphenol crystallization containing an aromatic alcohol sulfonate at more than 100 ppm by mass and not more than 1% by mass with respect to a bisphenol is preferably obtained by the same manner as described in the (Method 3) by reacting an aromatic alcohol with a ketone or an aldehyde in the presence of a sulfuric acid catalyst. Such a composition for bisphenol crystallization containing a specific amount of aromatic alcohol sulfonate can be obtained by, for example, setting the molar ratio of the sulfuric acid to the aromatic alcohol (the number of moles of the sulfuric acid/the number of moles of the aromatic alcohol) to 0.1 to 10 (preferably 0.3 to 5, more preferably 0.5 to 3), and performing the reaction at 0 to 80° C. (preferably 5 to 70° C., more preferably 10 to 60° C.) for 0.05 to 10 hours (preferably 0.1 to 5 hours).

Alternatively, the composition for bisphenol crystallization containing an aromatic alcohol sulfonate at more than 100 ppm by mass and not more than 1% by mass with respect to a bisphenol can be obtained by mixing a predetermined amount of the aromatic alcohol sulfonate with a commercially available bisphenol or the like.

<Use of Bisphenol Composition>

The bisphenol composition can be used as a component of, for example, a variety of thermoplastic resins such as polyether resins, polyester resins, polyarylate resins, polycarbonate resins, polyurethane resins, and acrylic resins, and a variety of thermosetting resins such as epoxy resins, unsaturated polyester resins, phenol resins, polybenzoxazine resins, and cyanate resins; as a curing agent; as an additive; or as a precursor thereof; to be used for various uses including optical materials, recording materials, insulating materials, transparent materials, electronic materials, adhesive materials, and heat-resisting materials. The bisphenol composition is also useful as a developer or a discoloration inhibitor for thermal recording materials and the like; or as an additive such as a microbicide or an antibacterial/antifungal agent.

Among these, from the viewpoint of giving favorable mechanical properties, use as a raw material (monomers) of a thermoplastic resin or a thermosetting resin is preferred. In particular, use as a raw material of a polycarbonate resin or an epoxy resin is more preferred. Use as a developer is also preferred. In particular, use in combination with a leuco dye or a color change temperature regulator is more preferred.

[Polycarbonate Resin and Production Method Therefor]

A polycarbonate resin using a bisphenol composition as a raw material, and a production method therefor are described below.

The polycarbonate resin as one embodiment of the present invention is a polycarbonate resin comprising an aromatic alcohol sulfonate at not less than 1 ppb by mass in a resin.

From the viewpoint of guaranteeing an excellent color tone, the content of the aromatic alcohol sulfonate in the resin is preferably not less than 1 ppb by mass, more preferably not less than 5 ppb by mass, still more preferably not less than 8 ppb by mass, especially preferably not less than 10 ppb by mass, and is not more than 1.0% by mass, preferably not more than 100 ppm by mass, more preferably not more than 80 ppm by mass, still more preferably not more than 50 ppm by mass.

As an index for evaluation of the color tone, the yellowness (also referred to as "YI value" or "yellowness index value") is available. It can be measured according to ASTM D1925. In the evaluation of the color tone of the polycarbonate resin, YI is preferably not more than 50, more preferably not more than 30, still more preferably not more than 20.

The polycarbonate resin using a bisphenol composition as a raw material can be produced by reacting the above-mentioned bisphenol composition, or a bisphenol obtained by the above-mentioned method of producing a bisphenol. The production can be carried out by, for example, a method in which the bisphenol composition and a diester carbonate such as diphenyl carbonate are subjected to transesterification reaction in the presence of an alkali metal compound and/or an alkaline earth metal compound. The transesterification reaction may be carried out by appropriately selecting a known method. One example using the bisphenol composition and diphenyl carbonate as raw materials is described below.

In the method of producing a polycarbonate resin, diphenyl carbonate is preferably used in an excess amount with respect to the bisphenol in the bisphenol composition. The amount of the diphenyl carbonate used with respect to the bisphenol is preferably large from the viewpoint of producing a polycarbonate resin having less terminal hydroxyl groups and achieving excellent thermal stability of the polymer, but preferably small from the viewpoint of increasing the transesterification reaction rate and easily producing a polycarbonate resin having a desired molecular weight. From these reasons, the amount of the diphenyl carbonate used with respect to 1 mol of the bisphenol is usually not less than 1.001 mol, preferably not less than 1.002 mol. The amount is usually not more than 1.3 mol, preferably not more than 1.2 mol.

Regarding the method of feeding the raw materials, the bisphenol composition and the diphenyl carbonate may be fed as solids, but it is preferred to melt one or both, and to feed it/them in a liquid state.

When a polycarbonate resin is produced by transesterification reaction of the diphenyl carbonate and the bisphenol, a transesterification catalyst is usually used. In the method of producing a polycarbonate resin, an alkali metal compound(s) and/or an alkaline earth metal compound(s) is/are preferably used as the transesterification catalyst. These may be used either individually, or as a random combination of two or more at an arbitrary ratio. Practically, an alkali metal compound(s) is/are preferably used.

The amount of the transesterification catalyst used with respect to 1 mol of the bisphenol or the diphenyl carbonate is usually not less than 0.05 μmol, preferably not less than 0.08 μmol, more preferably not less than 0.10 μmol, and is usually not more than 100 μmol, preferably not more than 50 μmol, more preferably not more than 20 μmol.

In cases where the amount of the transesterification catalyst is within the range described above, polymerization activity required for production of a polycarbonate resin having a desired molecular weight can be easily obtained, and a polycarbonate resin can be easily obtained with an excellent polymer color tone, without excessive branching of the polymer, and with excellent fluidity during molding.

For production of a polycarbonate resin by the above method, it is preferred to feed both raw materials continuously to a raw-material mixing vessel, and then to feed the resulting mixture and a transesterification catalyst continuously to a polymerization vessel.

Usually, in the production of the polycarbonate resin by transesterification, both materials fed to the raw-material mixing vessel are uniformly stirred, and then fed to the polymerization vessel where the transesterification catalyst is added, to produce a polymer.

A bisphenol produced by the above-described method of producing a bisphenol as one embodiment of the present invention is highly pure, and hardly shows coloring. Therefore, the bisphenol can be used in a method of producing a highly pure polycarbonate. For example, a highly pure polycarbonate can be obtained by the polycondensation of a bisphenol obtained by the production method of the present invention, with diphenyl carbonate in the presence of a transesterification catalyst.

EXAMPLES

The present invention is described below more concretely by way of Examples and Comparative Examples. However, the present invention is not limited by the following Examples as long as the spirit of the present invention is not spoiled.

Experiment I

[Raw Materials and Reagents]

As 2,2-bis(4-hydroxy-3-methylphenyl)propane (hereinafter referred to as "bisphenol C"), toluene, sodium hydroxide, potassium hydroxide, raw material sulfuric acid, dodecanethiol, methanol, acetone, and cesium carbonate, reagents manufactured by Wako Pure Chemical Industries, Ltd. were used. The concentration of cresol sulfonic acid contained in the bisphenol C was below the detection limit (less than 1 ppb) as described later. Here, in cases where no particular treatment is carried out for the subject to be measured, the detection limit is usually 1 ppb. However, by performing treatment such as concentration, the detection limit can be 0.1 ppb.

As sodium phenol sulfonate, a reagent from Tokyo Chemical Industry Co., Ltd. was used.

As a cresol sulfonic acid (which may be hereinafter referred to as "4-hydroxy-3-methylbenzenesulfonic acid" or "2-hydroxy-3-methylbenzenesulfonic acid) solution, a reagent manufactured by Kishida Chemical Co., Ltd. was used.

As diphenyl carbonate, a product manufactured by Mitsubishi Chemical Corporation was used.

[Analysis]

(Time of Disappearance of Bubbles on Oil-Water Interface)

The time of disappearance of bubbles on the oil-water interface was defined as the time required for the number of bubbles to become not more than 10 as observed by visually counting the bubbles on the interface. In the method of evaluation of the time of disappearance of bubbles on the oil-water interface, the time was rated as "S" in cases where the time was less than 10 minutes, "A" in cases where the time was not less than 10 minutes and less than 30 minutes, "B" in cases where the time was not less than 30 minutes and less than 1 hour, and "C" in cases where the time was not less than 1 hour.

(Qualitative and Quantitative Analysis of Sodium 4-Hydroxy-3-Methylbenzenesulfonate and Sodium 2-Hydroxy-3-Methylbenzenesulfonate)

Qualitative analysis of sodium 4-hydroxy-3-methylbenzenesulfonate and sodium 2-hydroxy-3-methylbenzenesulfonate was carried out by $^1$H-NMR and Na analysis by an ICP mass spectrometer.

The $^1$H-NMR (proton nuclear magnetic resonance ($^1$H NMR)) measurement was carried out using TYPE JNM=ECS400 manufactured by JEOL LTD.

The measurement of the sodium atom concentration was carried out by the following procedure. Nitric acid was added to bisphenol, and degradation was allowed to occur under pressurized and sealed conditions using a microwave degradation apparatus. The resulting degradation liquid was diluted with pure water, and subjected to measurement of the concentration of sodium atoms contained in the bisphenol using ELEMENT 2, manufactured by Thermo Fisher Scientific Inc.

Quantitative analysis of sodium 4-hydroxy-3-methylbenzenesulfonate and sodium 2-hydroxy-3-methylbenzenesulfonate was carried out by measurement with a high-performance liquid chromatograph-mass spectrometer by the following procedure under the following conditions based on a prepared calibration curve and the use of a standard substance.

High-performance liquid chromatograph apparatus: Agilent 1200, Capcellpak C18 MG3 3 µm 75 mm×4.6 mm ID Method: Low-pressure gradient method Analysis temperature: 40° C.

Eluent composition:
  Liquid A, 1 mmol/L aqueous ammonium formate solution acetic acid; Liquid B, acetonitrile
  At Minute 0 of the analysis time, Liquid A:Liquid B=99.5:0.5 (volume ratio, the same applies hereinafter).
  From Minute 0 to Minute 15 during the analysis time, the eluent composition was gradually changed to Liquid A:Liquid B=5:95.
  From Minute 15 to Minute 25 during the analysis time, the composition was maintained at Liquid A:Liquid B=5:95.
  The analysis was carried out at a flow rate of 1 mL/min.

Mass spectrometer: Agilent LC/MS 6130

Method: ESI (with use of an AJS probe)

(Bisphenol Production Rate)

The production rate of phenol in reaction of bisphenol C with diphenyl carbonate was analyzed by high-performance liquid chromatography (hereinafter referred to as LC) by the following procedure under the following conditions.

Apparatus:
  Column incubation vessel, CTO-10, manufactured by Shimadzu Corporation
  Detector, SPD-M10AVP, manufactured by Shimadzu Corporation
  Pump, LC-10AD, manufactured by Shimadzu Corporation Inertsil ODS-II 5 µm 150 mm×4.6 mm ID, manufactured by GL Sciences, Inc.

Method: isocratic method

Analysis temperature: 40° C.

Eluent composition water:acetonitrile=10:90 (volume ratio)

The analysis was carried out as follows.
- At Minute 0 of the analysis time, the pump flow rate was 0.5 mL/min.
- From Minute 0 to Minute 15 during the analysis time, the pump flow rate was gradually changed to 2 mL/min.
- From Minute 15 to Minute 30 during the analysis time, the pump flow rate was maintained at 2 mL/min.
- The detection wavelength was 210 nm.

As the abundance of components that inhibit reaction with diphenyl carbonate increases in the bisphenol C, the phenol production rate decreases, while as the components that inhibit the reaction decreases, the phenol production rate increases.

The phenol production rate (initial polymerization activity) was calculated according to the following equation.

Phenol production rate (initial polymerization activity)=LC area of phenol (LC area of phenol+LC area of diphenyl carbonate+LC area of bisphenol C)×100(%)

The LC area means the area of the peak detected by high-performance chromatography.

(Composition of Bisphenol C Production Reaction Liquid)

The composition analysis of the bisphenol C production reaction liquid was carried out by high-performance liquid chromatography by the following procedure under the following conditions.
- Apparatus: LC-2010A, Imtakt Scherzo SM-C18 3 μm 150 mm×4.6 mm ID, manufactured by Shimadzu Corporation
- Low-pressure gradient method
- Analysis temperature: 40° C.
- Eluent composition:
    - Liquid A, solution of ammonium acetate:acetic acid: demineralized water=3.000 g:1 mL:1 L
    - Liquid B, solution of ammonium acetate:acetic acid: acetonitrile=1.500 g:1 mL:900 mL
- At Minute 0 of the analysis time, Liquid A:Liquid B=60:40 (volume ratio, the same applies hereinafter).
- From Minute 0 to Minute 25 during the analysis time, the eluent composition was gradually changed to Liquid A:Liquid B=90:10.
- From Minute 25 to Minute 30 during the analysis time, the composition was maintained at Liquid A:Liquid B=90:10.
- The analysis was carried out at a flow rate of 0.8 mL/min.

(Reaction Yield of Bisphenol (in Terms of Acetone))

The reaction yield (mol %) of bisphenol C in terms of acetone was determined by calculating the bisphenol C concentration in the reaction liquid based on the peak detected at a wavelength of 280 nm by high-performance liquid chromatography, calculating, from the concentration, the molar amount of the bisphenol C contained in the bisphenol C production reaction liquid, and then performing the following calculation: the molar amount of the bisphenol C÷the molar amount of the raw material acetone×100%.

(Viscosity-Average Molecular Weight)

The viscosity-average molecular weight (Mv) was determined by dissolving the polycarbonate resin in methylene chloride (concentration, 6.0 g/L), measuring the specific viscosity ($\eta sp$) at 20° C. using an Ubbelohde viscosity tube, and then calculating the viscosity-average molecular weight (Mv) according to the following equations.

$$\eta sp/C=[\eta](1+0.28\eta sp)$$

$$[\eta]=1.23\times10^{-4}Mv^{0.83}$$

(Terminal-Hydroxyl-Group Concentration of Polycarbonate Resin)

The terminal-hydroxyl-group concentration (OH concentration) of the polycarbonate resin was measured by performing colorimetry according to the titanium tetrachloride/acetic acid method (see Makromol. Chem. 88, 215 (1965)).

(Pellet YI)

The pellet YI (transparency of the polycarbonate resin) was evaluated by measuring the YI value (yellowness index value) in the reflected light of the polycarbonate resin pellet according to ASTM D1925. The device used was CM-5, a spectrocolorimeter manufactured by Konica Minolta, Inc. The following measurement conditions were selected: measurement diameter, 30 mm; SCE. A calibration glass for petri-dish measurement CM-A212 was attached to the measurement section, and then covered with a zero-calibration box CM-A124, followed by performing zero calibration. Subsequently, white calibration was carried out using a built-in white calibration plate. Thereafter, measurement was carried out using a white calibration plate CM-A210 to confirm the following conditions: L*, 99.40±0.05; a*, 0.03±0.01; b*, −0.43±0.01; and YI, −0.58±0.01. The measurement of the pellet was carried out after packing the pellet in a cylindrical glass container having an inner diameter of 30 mm and a height of 50 mm to a depth of about 40 mm. An operation of removing the pellet from the glass container and then performing the measurement again was repeated twice, and the average of the values from the total of 3 times of measurement was used.

Reference Example 1

To a 1-L recovery flask equipped with a magnetic rotor, 242 g of a cresol sulfonic acid solution (composition: 63% by mass ortho-cresol sulfonic acid, 1.5% by mass cresol, 3% by mass sulfuric acid, and 32.5% water), 38.4 g of sodium hydroxide, and 32 g of demineralized water were placed, and the recovery flask was placed in an ice bath, followed by stirring. Complete dissolution of the sodium hydroxide in the recovery flask was confirmed to prepare 55.6% by mass sodium cresol sulfonate solution.

Reference Example 2

Part of the sodium cresol sulfonate solution obtained in Reference Example 1 was taken into a 500-mL recovery flask, and concentrated to dryness under reduced pressure using an evaporator equipped with an oil bath. Part of the resulting white solid was washed by suspension in 100 g of acetone, and then washed by suspension in 100 g of toluene, to obtain 1.5 g of sodium cresol sulfonate. Using the sodium cresol sulfonate, 2.3% by mass aqueous sodium cresol sulfonate solution was prepared.

Reference Example 3

Using sodium phenol sulfonate, 2.3% by mass aqueous sodium phenol sulfonate solution was prepared.

Reference Example 4

In a 1-L separable flask equipped with a condenser, a jacket, and an anchor-shaped stirring blade, 100 g of xylenol and 10 g of toluene were placed. Thereafter, 100 g of 98% sulfuric acid was slowly fed thereto, and the resulting mixture was stirred at 50° C. for 1 hour. Since the resulting reaction liquid was a slurry, filtration under reduced pressure was carried out. The resulting cake was placed in a 500-mL recovery flask, and toluene and 25% aqueous sodium hydroxide solution were added thereto while watching a pH meter until neutralization was achieved. The resulting slurry was filtered under reduced pressure, and the resulting cake was washed by suspension in toluene, followed by sprinkle-washing with water and drying with a rotary evaporator under reduced pressure, to obtain 10 g of a white solid. As result of NMR measurement of the resulting white solid, it was found to be xylenol sulfonic acid (which may be hereinafter referred to as 4-hydroxy-2,6-dimethylbenzenesulfonic acid), and the concentration of Na contained in the white solid was found to be 10% by mass according to ICP mass spectrometry. Thus, the white solid was sodium 4-hydroxy-2,6-dimethylbenzenesulfonate. Using the sodium xylenol sulfonate, 2.3% by mass aqueous sodium xylenol sulfonate solution was prepared.

Example 1

By addition of 4.7 g of a commercially available bisphenol C (manufactured by Wako Pure Chemical Industries, Ltd.) and 20 μL of the sodium cresol sulfonate solution prepared in Reference Example 2, a bisphenol C composition containing sodium cresol sulfonate at 100 ppm by mass with respect to bisphenol C was prepared.

In a Teflon (registered trademark) test tube, 4.7 g of the bisphenol C composition and 4.5 g of diphenyl carbonate were placed, and the resulting mixture was heated for 90 minutes on an aluminum block heater heated at 194° C. Part of the resulting reaction liquid was removed, and subjected to high-performance liquid chromatography to analyze the phenol production rate in the reaction with the diphenyl carbonate. As a result, production of phenol at 0.5% by area was found.

Example 2

By addition of 4.7 g of a commercially available bisphenol C and 20 μL of the sodium xylenol sulfonate solution prepared in Reference Example 4, a bisphenol C composition containing sodium xylenol sulfonate at 100 ppm by mass with respect to bisphenol C was prepared.

In a Teflon test tube, 4.7 g of the bisphenol C composition and 4.5 g of diphenyl carbonate were placed, and the resulting mixture was heated for 90 minutes on an aluminum block heater heated at 194° C. Part of the resulting reaction liquid was removed, and subjected to high-performance liquid chromatography to analyze the phenol production rate in the reaction with the diphenyl carbonate. As a result, production of phenol at 0.4% by area was found.

Example 3

By addition of 4.7 g of a commercially available bisphenol C and 20 μL of the sodium phenol sulfonate solution prepared in Reference Example 3, a bisphenol C composition containing sodium phenol sulfonate at 100 ppm by mass with respect to bisphenol C was prepared.

In a Teflon test tube, 4.7 g of the bisphenol C composition and 4.5 g of diphenyl carbonate were placed, and the resulting mixture was heated for 90 minutes on an aluminum block heater heated at 194° C. Part of the resulting reaction liquid was removed, and subjected to high-performance liquid chromatography to analyze the phenol production rate in the reaction with the diphenyl carbonate. As a result, production of phenol at 0.6% by area was found.

Example 4

By addition of 4.7 g of a commercially available bisphenol C, and 20 μL of an aqueous solution obtained by preparation of a sodium cresol sulfonate solution at a concentration of 230 ppm by mass with respect to the bisphenol C composition using the sodium cresol sulfonate solution prepared in Reference Example 2, a bisphenol C composition containing sodium cresol sulfonate at 1 ppb by mass with respect to bisphenol C was prepared.

In a Teflon test tube, 4.7 g of the bisphenol C composition and 4.5 g of diphenyl carbonate were placed, and the resulting mixture was heated for 90 minutes on an aluminum block heater heated at 194° C. Part of the resulting reaction liquid was removed, and subjected to high-performance liquid chromatography to analyze the phenol production rate in the reaction with the diphenyl carbonate. As a result, production of phenol at 0.3% by area was found.

Comparative Example 1

As a bisphenol C composition, a commercially available bisphenol C was used directly.

In a Teflon (registered trademark) test tube, 4.7 g of the bisphenol C composition, 4.5 g of diphenyl carbonate, and 20 μL aqueous potassium hydroxide solution of 33.7 μg/g were added, and the resulting mixture was heated for 90 minutes on an aluminum block heater heated at 194° C. Part of the resulting reaction liquid was removed, and subjected to high-performance liquid chromatography to analyze the phenol production rate in the reaction with the diphenyl carbonate. As a result, production of phenol at 0.1% by area was found.

For accurate determination of the content of aromatic alcohol sulfonate in the bisphenol, 10 g of the bisphenol C composition, 1.5 mL of ortho-xylene, and 1.0 mL of acetonitrile were added in a 10 mL glass centrifuge container, and completely being heated to dissolvement to provide a homogeneous solution. The resulting solution was allowed to cool to room temperature to obtain a solid. Thereafter, a glass filter and a receiver were arranged to provide a centrifugal tube, and a centrifuge was used (for 10 minutes at 2000 revolutions per minute) to extract 1 g of a liquid from the solid. After concentrating the bisphenol C composition as described above, analysis of the aromatic alcohol sulfonate was carried out. However, since the content was less than the detection limit of 0.1 ppb by mass, no aromatic alcohol sulfonate could be detected.

Comparative Example 2

By addition of 4.7 g of a commercially available bisphenol C and a dilution of a commercially available cresylic acid solution, a bisphenol C composition containing cresol sulfonic acid at 5 ppm by mass with respect to bisphenol C was prepared.

In a Teflon test tube, 4.7 g of the bisphenol C composition and 4.5 g of diphenyl carbonate were added, and the resulting mixture was heated for 90 minutes on an aluminum block heater heated at 194° C. Part of the resulting reaction liquid was removed, and subjected to high-performance liquid chromatography to analyze the phenol production rate in the reaction with the diphenyl carbonate. As a result, no production of phenol could be found.

Comparative Example 3

By addition of 4.7 g of a commercially available bisphenol C and a commercially available cresylic acid solution, a bisphenol C composition containing cresylic acid at 100 ppm by mass with respect to bisphenol C was prepared.

In a Teflon test tube, 4.7 g of the bisphenol C composition and 4.5 g of diphenyl carbonate were added, and the resulting mixture was heated for 90 minutes on an aluminum block heater heated at 194° C. Part of the resulting reaction liquid was removed, and subjected to high-performance liquid chromatography to analyze the phenol production rate in the reaction with the diphenyl carbonate. As a result, no production of phenol could be found.

For Examples 1 to 4 and Comparative Examples 1 to 3, the phenol production rate in the reaction with diphenyl carbonate is summarized in Table 1. Based on the comparison between Example 1 and Comparative Example 1, it shows that bisphenol C composition containing sodium cresol sulfonate shows a high initial polymerization activity (phenol production rate). Further, based on comparison of Example 1 or 4 and Comparative Example 2 or 3, it shows, in cases where the cresol sulfonic acid contained in the bisphenol C composition is sodium salt of cresol sulfonic acid, the initial polymerization activity is getting higher.

TABLE 1

|  | Aromatic alcohol sulfonate and its salt contained in bisphenol composition | | Phenol production rate in reaction with diphenyl carbonate |
| --- | --- | --- | --- |
|  | Type | Concentration |  |
| Example 1 | Sodium cresol sulfonate | 100 ppm by mass | 0.5% by area |
| Example 2 | Sodium xylenol sulfonate | 100 ppm by mass | 0.4% by area |
| Example 3 | Sodium phenol sulfonate | 100 ppm by mass | 0.6% by area |
| Example 4 | Sodium cresol sulfonate | 1 ppb by mass | 0.3% by area |
| Comparative Example 1 | Cresol sulfonic acid | Less than 0.0001 ppm by mass (less than 0.1 ppm by mass) | 0.1% by area |
| Comparative Example 2 | Cresol sulfonic acid | 5 ppm by mass | ※1 |
| Comparative Example 3 | Cresol sulfonic acid | 100 ppm by mass | ※1 |

※1 No phenol was found produced.

Example 5

(Production of Composition for Bisphenol Crystallization)

In a 1 L separable flask equipped with a condenser, a jacket, and an anchor-shaped stirring blade, 100 g of a commercially available bisphenol C and 0.18 g of the sodium cresol sulfonate solution prepared in Reference Example 1 were added to prepare a bisphenol C composition containing 0.1% by mass of sodium ortho-cresol sulfonate.
(Production of Bisphenol Composition)

To the separable flask, 163 g of toluene was added. The resulting mixture was heated to 80° C. to provide a homogeneous solution. To the homogeneous solution, 40 g of demineralized water was added, and the resulting mixture was mixed for 10 minutes while the temperature was kept at 80° C. Thereafter, the mixture was left to stand to allow oil-water separation.

The time of disappearance of bubbles on the oil-water interface was 1 minute 34 seconds. Thereafter, the aqueous phase was removed from the separable flask to obtain the organic phase.

The organic phase obtained was cooled from 80° C. to 10° C. to allow crystallization of bisphenol C. By performing solid-liquid separation using a centrifuge, a bisphenol C of wet state was obtained.

The bisphenol C in a wet state was placed in a 1 L recovery flask, and dried under reduced pressure using a rotary evaporator equipped with a water bath of 80° C., followed by washing with water and drying, then 95 g of a bisphenol C composition was obtained.

Part of the bisphenol C composition was removed, and subjected to analysis of the amounts of sodium 4-hydroxy-3-methylbenzenesulfonate and sodium 2-hydroxy-3-methylbenzenesulfonate using a high-performance liquid chromatograph-mass spectrometer. As a result, sodium 4-hydroxy-3-methylbenzenesulfonate was found to be contained at 35 ppm by mass, and sodium 2-hydroxy-3-methylbenzenesulfonate was found to be contained at 2 ppm by mass.
(Measurement of Phenol Production Rate)

In a Teflon (registered trademark) test tube, 4.7 g of the bisphenol C composition after the washing with water and the drying, 4.5 g of diphenyl carbonate, and 20 μL of 33.7 ppm by mass aqueous potassium hydroxide solution were added, and the resulting mixture was heated for 90 minutes on an aluminum block heater heated at 194° C. Part of the resulting reaction liquid was removed, and subjected to high-performance liquid chromatography to analyze the phenol production rate in the reaction with the diphenyl carbonate. As a result, production of phenol at 1.2% by area was found.

Example 6

The same operation as in Example 5 was carried out except that the production lot of the commercially available bisphenol C used in the present Example was different from that of the commercially available bisphenol C used in Example 5. Part of the resulting reaction liquid was removed, and subjected to high-performance liquid chromatography to analyze the phenol production rate in the reaction with the diphenyl carbonate. As a result, production of phenol at 1.2% by area was found.

Example 7

The same operation as in Example 5 was carried out except that the production lot of the commercially available bisphenol C used in the present Example was different from those of the bisphenol C used in Examples 5 and 6. Part of the resulting reaction liquid was removed, and subjected to high-performance liquid chromatography to analyze the phenol production rate in the reaction with the diphenyl carbonate. As a result, production of phenol at 1.2% by area was found.

Comparative Example 4

In a 1 L separable flask equipped with a condenser, a jacket, and an anchor-shaped stirring blade, 100 g of a commercially available bisphenol C and 163 g of toluene were added. The resulting mixture was heated to 80° C. to provide a homogeneous solution. To the homogeneous solution, 40 g of demineralized water was added, and the resulting mixture was mixed for 10 minutes while the temperature was kept at 80° C. Thereafter, the mixture was left to stand to allow oil-water separation. The bubbles on the oil-water interface did not disappear even after 5 hours. The aqueous phase was removed from the separable flask, and the organic phase, in a state where a small amount of bubble was still contained, was cooled from 80° C. to 10° C. to allow crystallization of bisphenol C. By performing solid-liquid separation using a centrifuge, a bisphenol C of wet state was obtained. The bisphenol C in a wet state was placed in a 1 L recovery flask, and dried under reduced pressure using a rotary evaporator equipped with a water bath of 80° C., followed by washing with water and drying, to obtain 96 g of bisphenol C.

In a Teflon (registered trademark) test tube, 4.7 g of the bisphenol C, 4.5 g of diphenyl carbonate, and 20 µL of 33.7 ppm by mass aqueous potassium hydroxide solution were added, and the resulting mixture was heated for 90 minutes on an aluminum block heater heated at 194° C. Part of the resulting reaction liquid was removed, and subjected to high-performance liquid chromatography to analyze the phenol production rate in the reaction with the diphenyl carbonate. As a result, production of phenol at 0.2% by area was found.

For accurate determination of the content of aromatic alcohol sulfonate in the bisphenol, 10 g of the bisphenol C composition, 1.5 mL of ortho-xylene, and 1.0 mL of acetonitrile were placed in a 10 mL glass centrifuge container, and completely heated to dissolvement to provide a homogeneous solution. The resulting solution was allowed to cool to room temperature to obtain a solid. Thereafter, a glass filter and a receiver were arranged to provide a centrifugal tube, and a centrifuge was used (for 10 minutes at 2000 revolutions per minute) to extract 1 g of a liquid from the solid. After concentrating the bisphenol C composition as described above, analysis of the aromatic alcohol sulfonate was carried out. However, since the content was less than the detection limit of 0.1 ppb by mass, no aromatic alcohol sulfonate was detected.

For Examples 5 to 7 and Comparative Example 4, the amount of sodium cresol sulfonate (total amount of sodium 4-hydroxy-3-methylbenzenesulfonate and sodium 2-hydroxy-3-methylbenzenesulfonate) contained in the composition for bisphenol crystallization (bisphenol C before washing (washing with water and crystallization)), the time of disappearance of bubbles on the oil-water interface, the amount of sodium cresol sulfonate (total amount of sodium 4-hydroxy-3-methylbenzenesulfonate and sodium 2-hydroxy-3-methylbenzenesulfonate)) contained in the bisphenol composition (bisphenol C after washing (washing with water, crystallization, and drying)), and the phenol production rate in the reaction with diphenyl carbonate are summarized in Table 2.

As shown by Example 5, when the composition for bisphenol crystallization was obtained by addition of sodium salt of cresol sulfonic acid, and then a bisphenol C composition was obtained by washing (washing with water and crystallization), the time of disappearance of bubbles on the oil-water interface was short. Thus, it shows that sodium salt of cresol sulfonic acid functions as a surfactant. Further, in Example 5, the phenol production rate in the reaction with diphenyl carbonate was higher than that in Example 1. This can be assumed to due to the effect of the catalytic action that allowed the reaction with diphenyl carbonate to proceed, and also due to the fact that, since washing was carried out after obtaining the composition for bisphenol crystallization by addition of sodium cresol sulfonate, components that inhibit the reaction with diphenyl carbonate, contained in the bisphenol C composition, could be efficiently removed.

Further, according to Examples 5 to 7, even in cases where bisphenol C in different production lots are used as raw materials, components that inhibit the reaction with diphenyl carbonate, contained in the bisphenol C, can be similarly removed by performing the washing after the production of the crude bisphenol product by adding cresol sulfonic acid. Thus, bisphenol C compositions with stable quality can be stably produced. Further, based on the results on the phenol production rate in the reaction with diphenyl carbonate in Examples 5 to 7, it can be seen that reaction with diphenyl carbonate can be stably carried out with the resulting bisphenol C compositions.

Comparative Example 4 is a case where bisphenol C was produced by the same method as in Examples 5 to 7 except that a commercially available bisphenol C was used while not preparing a composition for bisphenol crystallization by addition of sodium cresol sulfonate to the commercially available bisphenol C. According to Comparative Example 4, it can be seen that the phenol production rate in the reaction with diphenyl carbonate is low even in a case where the bisphenol C is obtained by washing (washing with water and crystallization) of a commercially available bisphenol C, and hence the components that inhibit the reaction cannot be sufficiently removed by the washing in this case.

TABLE 2

| | Amount of sodium cresol sulfonate contained in composition for bisphenol crystallization (ppm by mass) | Time of disappearance of bubbles on oil-water interface | Amount of sodium cresol sulfonate contained in bisphenol composition (ppm by mass) | Phenol production rate in reaction with diphenyl carbonate |
|---|---|---|---|---|
| Example 5 | 1000 | S | 37 | 1.2% by area |
| Example 6 | 1000 | S | 35 | 1.2% by area |
| Example 7 | 1000 | S | 40 | 1.2% by area |
| Comparative Example 4 | (<0.0001) | C | <0.0001 | 0.2% by area |

Example 8

(Production of Composition for Bisphenol Crystallization)

In a full-jacket type 1 L separable flask equipped with a thermometer, a stirrer, and a 100 mL dropping funnel, 35.0 g (1.1 mol) of methanol was added under a nitrogen atmosphere, and then 77.7 g (0.7 mol) of 88% by weight raw material sulfuric acid was slowly added thereto. Thereafter, 72.6 g of toluene and 255.0 g (2.4 mol) of ortho-cresol and 7.3 g (0.04 mol) of dodecanethiol were added in the separable flask, followed by setting the temperature in the separable flask to 50° C. In the dropping funnel, 57.0 g (1.0 mol) of acetone was added, and it was slowly fed dropwise to the separable flask for 30 minutes. Upon completion of the dropwise addition of acetone, the reaction liquid had an orange color. The reaction liquid was reacted for 15 hours at 50° C.

After completion of the reaction, 135.0 g of toluene and 175.5 g of demineralized water were fed, and the temperature was increased to 80° C. After the temperature reached 80° C., the reaction liquid was left to stand to confirm that the precipitates generated during the reaction were dissolved into the organic phase and the aqueous phase. This was followed by extraction of the aqueous phase, which corresponded to the lower phase. Thereafter, saturated sodium hydrogen carbonate solution was added to the obtained organic phase to allow neutralization, followed by confirming that the pH of the aqueous phase, which corresponded to the lower phase, became not less than 9. After extraction of the aqueous phase, which corresponded to the lower phase, demineralized water was added to the obtained organic phase, and the resulting mixture was stirred for 10 minutes. Thereafter, the mixture was left to stand, and the aqueous phase was extracted.

Part of the obtained organic phase was removed, and subjected to high-performance liquid chromatography to analyze the amount of bisphenol C produced. As a result, the reaction yield in terms of acetone was found to be 85 mol %.

The organic phase was cooled from 80° C. to 30° C., and, when the temperature reached 30° C., 1 g of seed crystal bisphenol C was added thereto, followed by confirmation of precipitation. Thereafter, the mixture was cooled to 10° C., and, after the temperature reached 10° C., filtration was carried out under reduced pressure using a glass filter, to obtain 239.9 g of a composition for bisphenol C crystallization as a wet cake.

Part of the composition for bisphenol C crystallization was removed, and subjected to analysis of the amounts of sodium 4-hydroxy-3-methylbenzenesulfonate and sodium 2-hydroxy-3-methylbenzenesulfonate using a high-performance liquid chromatograph-mass spectrometer. As a result, sodium 4-hydroxy-3-methylbenzenesulfonate was found to be contained at 35 ppm by mass, and sodium 2-hydroxy-3-methylbenzenesulfonate was found to be contained at 160 ppm by mass.

(Production of Bisphenol Composition)

In a full-jacket type 1l, separable flask equipped with a thermometer and a stirrer, the whole amount of the composition for bisphenol C crystallization and 449 g of toluene were added, and the temperature was increased to 80° C. After confirming that the mixture became a homogeneous solution, the organic phase was sufficiently washed twice with 600 g of demineralized water. The time of disappearance of bubbles on the oil-water interface was about 5 minutes.

The obtained organic phase was cooled from 80° C. to 10° C. Thereafter, filtration was carried out using a centrifuge (for 10 minutes at 3000 revolutions per minute) to obtain a pure bisphenol C of wet state. Using an evaporator equipped with an oil bath, a low-boiling fraction was evaporated under reduced pressure at an oil bath temperature of 100° C., to obtain 180.9 g of a bisphenol C composition.

In a 10 mL glass centrifuge container, 10 g of the bisphenol C composition, 1.5 mL of ortho-xylene, and 1.5 mL of acetonitrile were added, and the resulting mixture was heated to allow complete dissolution, to provide a homogeneous solution. The solution was then allowed to cool to room temperature to obtain a solid. Thereafter, a glass filter and a receiver were arranged to the glass container to provide a centrifugal tube, and a centrifuge was used (for 10 minutes at 2000 revolutions per minute) to extract 1 g of a liquid from the solid. Part of the obtained liquid was removed, and subjected to analysis of the amounts of sodium 4-hydroxy-3-methylbenzenesulfonate and sodium 2-hydroxy-3-methylbenzenesulfonate using a high-performance liquid chromatograph-mass spectrometer. As a result, sodium 4-hydroxy-3-methylbenzenesulfonate was found to be contained at 5 ppb by mass, and sodium 2-hydroxy-3-methylbenzenesulfonate was found to be contained at 3 ppb by mass.

(Measurement of Phenol Production Rate)

In a Teflon (registered trademark) test tube, 4.7 g of the obtained bisphenol C composition, 4.5 g of diphenyl carbonate, and 20 µL of 33.7 ppm by mass aqueous potassium hydroxide solution were added, and the resulting mixture was heated for 90 minutes on an aluminum block heater heated at 194° C. Part of the resulting reaction liquid was removed, and subjected to high-performance liquid chromatography to analyze the initial polymerization activity. As a result, production of phenol at 1.6% by area was found.

(Production of Polycarbonate Resin)

In a glass reaction vessel with a capacity of 150 mL equipped with a stirrer and a distillate tube, 100.00 g (0.39 mol) of the bisphenol C composition, 86.49 g (0.4 mol) of diphenyl carbonate, and 479 µL of 400 ppm by mass aqueous cesium carbonate solution were added. The pressure in the glass reaction vessel was reduced to about 100 Pa, and then the pressure was restored to atmospheric pressure with nitrogen. By repeating this operation three times, the atmosphere in the reaction vessel was replaced with nitrogen. Thereafter, the reaction vessel was immersed in an oil bath at 200° C. to allow dissolution of the content. After setting the rotation speed of the stirrer to 100 revolutions per minute, the pressure in the reaction vessel was reduced from 101.3 kPa to 13.3 kPa in terms of the absolute pressure for 40 minutes while the phenol in the reaction vessel as by-product of oligomerization reaction between bisphenol C and diphenyl carbonate was evaporated. Subsequently, while the pressure in the reaction vessel was kept at 13.3 kPa, and while the phenol was further evaporated, transesterification reaction was carried out for 80 minutes. Thereafter, the external temperature of the reaction vessel was increased to 250° C., and the pressure in the reaction vessel was reduced from 13.3 kPa to 399 Pa in terms of the absolute pressure for 40 minutes to remove the distilled phenol to the outside of the system. Thereafter, the external temperature of the reaction vessel was increased to 280° C., and the absolute pressure in the reaction vessel was reduced to 30 Pa, followed by performing polycondensation reaction. When the stirring power of the stirrer in the reaction vessel reached a predetermined level, the polycondensation reaction was stopped. Subsequently, the pressure in the reaction vessel was restored with nitrogen to 101.3 kPa in terms of the absolute pressure, and then the pressure was increased to 0.2 MPa in terms of the gauge pressure, followed by extracting a polycarbonate in a strand shape from the bottom of the reaction vessel, to obtain a polycarbonate resin having the strand shape. Thereafter, using a rotary cutter, the strand was pelletized to obtain a polycarbonate resin having a pellet shape.

The viscosity-average molecular weight (Mv) of the polycarbonate was 24,800, and the terminal-hydroxyl-group concentration (OH concentration) was 769 ppm by mass. The pellet YI was 7.62.

Part of the polycarbonate was subjected to measurement of the Na concentration using an ICP mass spectrometer. The concentration detected was 0.1 ppm by mass.

(Content of Aromatic Alcohol Sulfonate in Polycarbonate Resin)

To a 50 mL Erlenmeyer flask equipped with a stirring bar, 0.2 g of the obtained polycarbonate and 1 mL of methylene chloride were added, followed by allowing dissolution. Thereafter, with sufficient stirring, 4 mL of methanol was slowly added dropwise thereto. After completion of the dropwise addition, the Erlenmeyer flask was immersed in a water bath, followed by allowing extraction for 30 minutes. The whole resulting solution was collected into a 15 mL centrifuge tube, and centrifugation was carried out at 5000 revolutions per minute for 15 minutes. Thereafter, 3 mL of the supernatant was collected into a 50 mL recovery flask. The 50 mL recovery flask was arranged to a rotary evaporator equipped with a water bath, and the water bath was operated at 45° C. to evaporate the supernatant to dryness. To the dried product obtained by the evaporation to dryness, 0.5 mL of methanol was added. After tight sealing, ultrasonic extraction was carried out for 5 minutes. Part of the resulting solution was analyzed using a high-performance liquid chromatograph-mass spectrometer. As a result, 3 ppb by mass 2-hydroxy-3-methylbenzenesulfonate was detected. Since the amount in terms of Na contained in the polycarbonate is larger than the amount of 2-hydroxy-3-methylbenzenesulfonic acid contained in the polycarbonate, the 2-hydroxy-3-methylbenzenesulfonic acid contained in the polycarbonate is sodium 2-hydroxy-3-methylbenzenesulfonate, and its concentration is 3 ppb by mass (3 ppb by mass=molecular weight of 2-hydroxy-3-methylbenzenesulfonic acid 188.2 g/mol×sodium 2-hydroxy-3-methylbenzenesulfonate 210.2 g/mol).

Experiment 2

[Raw Materials and Reagents]

As ortho-cresol, a special grade reagent manufactured by Wako Pure Chemical Industries, Ltd. or a product manufactured by Nippon Steel Chemical Co., Ltd. was used.

As acetone and methanol, special grade reagents manufactured by Wako Pure Chemical Industries, Ltd. or products manufactured by Daishin Chemical Co., Ltd. were used.

As dodecanethiol, a special grade reagent manufactured by Wako Pure Chemical Industries, Ltd. or a product manufactured by Kao Corporation was used.

As toluene, a special grade reagent manufactured by Wako Pure Chemical Industries, Ltd. or a product manufactured by Cosmo Oil Co., Ltd. was used.

As sulfuric acid, a special grade reagent manufactured by Wako Pure Chemical Industries, Ltd. or a product manufactured by Kaname Chemicals Co., Ltd. was used.

As acetonitrile, acetic acid, ammonium acetate, ethyl acetate, ortho-xylene, para-xylene, xylene, mesitylene, chlorobenzene, isopropyl alcohol, 1-octanol, ethylene glycol, 2,6-xylenol, phenol, dodecanal, cyclohexanone, cycloheptanone, methyl ethyl ketone, methyl isobutyl ketone, 3.3.5-trimethylcyclohexanone, sodium hydroxide, sodium hydrogen carbonate, acetophenone, deuterated chloroform, heptane, cesium carbonate, 2,2-bis(4-hydroxy-3-methylphenyl)propane, 9,9-bis(4-hydroxy-3-methylphenyl)fluorene, and 2,2-bis(4-hydroxy-3,5-dimethylphenyl)propane, special grade reagents manufactured by Wako Pure Chemical Industries, Ltd. were used.

As 3-mercaptopropionic acid, fluorenone, 2-ethylhexanal, 2-phenylphenol, 2-cyclohexylphenol, 2-cyclohexylphenol, and 2-benzylphenol, reagents manufactured by Tokyo Chemical Industry Co., Ltd. were used.

As 2,2-bis(4-hydroxyphenyl) propane and diphenyl carbonate, a product manufactured by Mitsubishi Chemical Corporation was used.

As 1,1-bis(4-hydroxyphenyl) dodecane, a product manufactured by Shinryo Corporation was used.

[Analysis]

Analysis of monomethyl sulfate and mono(2-hydroxyethyl) sulfate was carried out by measurement using proton nuclear magnetic resonance PH NMR). The proton nuclear magnetic resonance PH NMR) measurement was carried out using the JNM=ECS400 type manufactured by JEOL LTD.

Analysis of the produced bisphenol was carried out by measurement using high-performance liquid chromatograph-mass spectrometry (LCMS). The high-performance liquid chromatograph-mass spectrometry (LCMS) was carried out by the following procedure under the following conditions.

(Separation Apparatus): Agilent 1200, Imtakt Scherzo SM-C18 3 µm 150 mm×4.6 mm ID, manufactured by Agilent Technologies, Inc. Low-pressure gradient method. Analysis temperature, 40° C. Eluent composition: Liquid A, solution of ammonium acetate:acetic acid:demineralized water=3.000 g:1 mL:1 L. Liquid B, solution of ammonium acetate:acetic acid:acetonitrile=1.500 g:1 mL:1000 mL. At Minute 0 of the analysis time, Liquid A:Liquid B=60:40 (volume ratio, the same applies hereinafter). From Minute 0 to Minute 25 during the analysis time, the eluent composition was gradually changed to Liquid A:Liquid B=90:10. From Minute 25 to Minute 30 during the analysis time, the composition was maintained at Liquid A:Liquid B=90:10. The analysis was carried out at a flow rate of 1.0 mL/min. The detection wavelength was 280 nm.

(Mass Spectrometer): Agilent LC/MS 6130, manufactured by Agilent Technologies, Inc. As an ion source, an ESI (Positive/Negative) AJS probe was used.

Composition analysis of the bisphenol reaction liquid was carried out by high-performance liquid chromatography by the following procedure under the following conditions.

(Apparatus): LC-2010A, Imtakt Scherzo SM-C18 3 µm 150 mm×4.6 mm ID, manufactured by Shimadzu Corporation. Low-pressure gradient method. Analysis temperature, 40° C. Eluent composition: Liquid A, solution of ammonium acetate:acetic acid:demineralized water=3.000 g:1 mL:1 L. Liquid B, solution of ammonium acetate:acetic acid:acetonitrile=1.500 g:1 mL:900 mL. At Minute 0 of the analysis time, Liquid A:Liquid B=60:40 (volume ratio, the same applies hereinafter). From Minute 0 to Minute 25 during the analysis time, the eluent composition was gradually changed to Liquid A:Liquid B=90:10. From Minute 25 to Minute 30 during the analysis time, the composition was maintained at Liquid A:Liquid B=90:10. The analysis was carried out at a flow rate of 0.8 mL/min. The detection wavelength was 280 nm.

The reaction yield (mol %) in terms of acetone was determined by calculating the molar amount of bisphenol contained in the reaction liquid based on the analysis value of bisphenol obtained by high-performance liquid chromatography, and then performing the following calculation: the molar amount of the bisphenol÷the molar amount of the raw material acetone×100%.

The reaction yield (% by area) (also referred to as "production rate") of isopropylcresol dimer was calculated as follows: the area of isopropylcresol dimer obtained by high-performance liquid chromatography÷the area of 2,2-bis(4-hydroxy-3-methylphenyl) propane×100 (% by area). Further, the production rates (% by area) of substances other than isopropylcresol dimer can be similarly calculated by the method.

The yield (mol %) in terms of acetone according to the present invention was calculated as follows: the molar amount of the obtained bisphenol the molar amount of the raw material acetone×100%.

Reference Example 5

To a 50 mL recovery flask, 0.2 g of methanol was taken, and 0.5 g of 92% by weight sulfuric acid was slowly added thereto. The resulting mixture was mixed by shaking for 1 minute. This liquid was added in a 5-mm diameter NMR test tube, and a deuterated chloroform tube (2-mm diameter sealed tube) for locking was inserted into the sample, followed by $^1$H NMR measurement. On the $^1$H NMR spectrum, a signal was found at δ 4.0 ppm. When 9.7 mg of reagent sodium monomethyl sulfate was added to the NMR test tube, the peak at δ 4.0 ppm increased. Thus, the peak was confirmed to be a signal of a proton of monomethyl sulfate. From this result, it could be confirmed that monomethyl sulfate is produced by mixing of sulfuric acid with methanol.

Reference Example 6

To a 50 mL recovery flask, 0.2 g of ethylene glycol was taken, and 0.5 g of 92% by weight sulfuric acid was slowly added thereto. The resulting mixture was mixed by shaking for 1 minute. This liquid was placed in a 5 mm diameter NMR test tube, and a deuterated chloroform tube (2-mm diameter sealed tube) for locking was inserted into the sample, followed by $^1$H NMR measurement. On the $^1$H NMR spectrum, broad signals which were thought to be derived from (2-hydroxyethyl) sulfate were detected at δ 3.98-3.99 ppm and 4.19-4.21 ppm. From this result, it could be confirmed that mono(2-hydroxyethyl) sulfate is produced by mixing of sulfuric acid with ethylene glycol.

Example 9

In a full-jacket type 1 L separable flask equipped with a thermometer, a stirrer, and a 100 mL dropping funnel, 35.0 g (1.1 mol) of methanol was added under a nitrogen atmosphere, and then 77.7 g (0.7 mol) of 88% by weight sulfuric acid was slowly added thereto. Part of the resulting solution was removed, and put in a 5 mm diameter NMR test tube, and a deuterated chloroform tube (2 mm diameter sealed tube) for locking was inserted into the sample, followed by $^1$H NMR measurement. On the $^1$H NMR spectrum, a signal was found at δ 4.0 ppm. Thus, production of monomethyl sulfate could be confirmed. Further, based on the integrated values for δ 4.0 ppm, which belongs to monomethyl sulfate, and the peak belonging to methanol, the amount of monomethyl sulfate produced was calculated. As a result, the amount of monomethyl sulfate produced was found to be 30% by weight. Thereafter, 72.6 g of toluene was placed in a reactor, and 255.0 g (2.4 mol) of ortho-cresol and 7.3 g (0.04 mol) of dodecanethiol were placed in the separable flask, followed by setting the temperature in the separable flask to 50° C. In the dropping funnel, 57.0 g (1.0 mol) of acetone was placed, and it was slowly fed dropwise to the separable flask for 30 minutes. Upon completion of the dropwise addition of acetone, the reaction liquid had an orange color. The reaction liquid was reacted for 15 hours at 50° C. After completion of the reaction, 135.0 g of toluene and 175.5 g of demineralized water were fed, and the temperature was increased to 80° C. After the temperature reached 80° C., the reaction liquid was left to stand to confirm that the precipitates generated during the reaction were dissolved into the organic phase and the aqueous phase. This was followed by extraction of the aqueous phase in lower layer. Thereafter, saturated sodium hydrogen carbonate solution was added to the obtained organic phase to allow neutralization, followed by confirming that the pH of the aqueous phase in the lower layer, became not less than 9. After extraction of the aqueous phase in the lower layer, demineralized water was added to the obtained organic phase, and the resulting mixture was stirred for 10 minutes. Thereafter, the mixture was left to stand, and the aqueous phase was extracted. Part of the obtained organic phase was removed, and subjected to high-performance liquid chromatography to analyze the amount of bisphenol C produced. As a result, the reaction yield in terms of acetone was found to be 85 mol %. Further, a peak found at a retention time of 15.7 minutes in the high-performance liquid chromatograph was subjected measurement by high-performance liquid chromatograph-mass spectrometry in the negative mode. As a result, a mass number of 295 (M$^+$-1) was found, and therefore the peak at the retention time of 15.7 minutes was found to be isopropenyl cresol dimer. The production rate of the isopropenyl cresol dimer was 0.7% by area. The organic phase was cooled from 80° C. to 30° C., and, when the temperature reached 30° C., 1 g of seed crystal 2,2-bis(4-hydroxy-3-methylphenyl) propane (hereinafter referred to as bisphenol C) was added thereto, followed by confirmation of precipitation. Thereafter, the mixture was cooled to 10° C., and, after the temperature reached 10° C., filtration was carried out under reduced pressure using a glass filter, to obtain 239.9 g of crude bisphenol C as a wet cake.

In a full-jacket type 1 L separable flask equipped with a thermometer and a stirrer, the whole amount of the crude bisphenol C and 449 g of toluene were placed, and the temperature was increased to 80° C. After conforming formation of a homogeneous solution, the solution was cooled to 10° C. Thereafter, filtration was carried out under reduced pressure using a glass filter, to obtain a wet pure bisphenol C. Using an evaporator equipped with an oil bath, a low-boiling fraction was evaporated under reduced pressure at an oil bath temperature of 100° C., to obtain 180.9 g (0.7 mol; yield in terms of acetone, 72 mol %) of a bisphenol C.

Example 10

In a full-jacket type 1.5 L separable flask equipped with a thermometer, a stirrer, and a dropping funnel, 0.1 g (3.1 mmol) of methanol was added under a nitrogen atmosphere, and then 250 g (0.7 mol) of 80% by weight sulfuric acid was slowly added thereto. Part of the resulting solution was removed and subjected to measurement of the $^1$HNMR spectrum. As a result, production of 10 wt ppm monomethyl sulfate was found. Thereafter, 320 g of toluene was added in a reactor, and 230.0 g (2.1 mol) of ortho-cresol was added in the separable flask, followed by setting the temperature in the separable flask to 30° C. In the dropping funnel, 51.0 g (0.9 mol) of acetone and 5.3 g (0.03 mol) of dodecanethiol were added, and these were slowly fed dropwise to the separable flask for 60 minutes while the internal temperature was maintained at 30° C. Upon completion of the dropwise addition of the mixture of acetone and dodecanethiol, the reaction liquid had an orange color. The resulting reaction liquid was mixed at 30° C. for 1 hour, and the temperature was then increased to 45° C. to allow the reaction to proceed. After the temperature reached 45° C. (completion of the reaction), 175.5 g of demineralized water and 135 g of 28% aqueous sodium hydroxide solution were fed thereto, followed by increasing the temperature to 80° C. After the temperature reached 80° C., the reaction liquid was left to stand to confirm that the precipitates generated during the reaction were dissolved into the organic phase and the aqueous phase. This was followed by extraction of the aqueous phase in the lower layer. Thereafter, saturated sodium hydrogen carbonate solution was added to the obtained organic phase to allow neutralization, followed by confirming that the pH of the aqueous phase in the lower layer, became not less than 9. After extraction of the aqueous phase in the lower layer, demineralized water was added to the obtained organic phase, and the resulting mixture was stirred for 10 minutes. Thereafter, the mixture was left to stand, and the aqueous phase was extracted. Part of the obtained organic phase was removed, and subjected to high-performance liquid chromatography to analyze the amount of bisphenol C produced. As a result, the reaction yield in terms of acetone was found to be 69 mol %. The production rate of isopropenyl cresol dimer was 0.24% by area.

Example 11

In a full-jacket type 1.5 L separable flask equipped with a thermometer, a stirrer, and a dropping funnel, 12 g (3.1 mmol) of methanol was added under a nitrogen atmosphere, and then 250 g (0.7 mol) of 80% by weight sulfuric acid was slowly added thereto. Part of the resulting solution was removed and subjected to measurement of the $^1$H NMR spectrum. As a result, production of 0.1 wt % monomethyl sulfate was found. Thereafter, 320 g of toluene was added in a reactor, and 230.0 g (2.1 mol) of ortho-cresol was added in the separable flask, followed by setting the temperature in the separable flask to 30° C. In the dropping funnel, 51.0 g (0.9 mol) of acetone and 5.3 g (0.03 mol) of dodecanethiol were added, and these were slowly fed dropwise to the separable flask for 60 minutes while the internal temperature was maintained at 30° C. Upon completion of the dropwise addition of the mixture of acetone and dodecanethiol, the reaction liquid had an orange color. The resulting reaction liquid was mixed at 30° C. for 1 hour, and the temperature was then increased to 45° C. to allow the reaction to proceed. After the temperature reached 45° C. (completion of the reaction), 175.5 g of demineralized water and 135 g of 28% aqueous sodium hydroxide solution were fed thereto, followed by increasing the temperature to 80° C. After the temperature reached 80° C., the reaction liquid was left to stand to confirm that the precipitates generated during the reaction were dissolved into the organic phase and the aqueous phase. This was followed by extraction of the aqueous phase in the lower layer. Thereafter, saturated sodium hydrogen carbonate solution was added to the obtained organic phase to allow neutralization, followed by confirming that the pH of the aqueous phase in the lower layer, became not less than 9. After extraction of the aqueous phase in the lower layer, demineralized water was added to the obtained organic phase, and the resulting mixture was stirred for 10 minutes. Thereafter, the mixture was left to stand, and the aqueous phase was extracted. Part of the obtained organic phase was removed, and subjected to high-performance liquid chromatography to analyze the amount of bisphenol C produced. As a result, the reaction yield in terms of acetone was found to be 63 mol %. The production rate of isopropenyl cresol dimer was 0.13% by area.

Comparative Example 5

In a full-jacket type 1 L separable flask equipped with a thermometer, a stirrer, and a 100 mL dropping funnel, 58.5 g (0.6 mol) of 92% by weight sulfuric acid, 54.3 g of toluene, 191.5 g (1.8 mol) of ortho-cresol, and 5.5 g (0.03 mol) of dodecanethiol were added under a nitrogen atmosphere, and the temperature in the separable flask was set to 50° C. In the dropping funnel, 42.5 g (0.7 mol) of acetone was added, and it was slowly fed dropwise to the separable flask for 30 minutes. Upon completion of the dropwise addition of acetone, the reaction liquid had a red-brown color. When the reaction liquid was allowed to react for 30 minutes at 50° C., the reaction liquid became completely solidified, and its mixing became impossible. Thereafter, 100 g of demineralized water and 200 g of ethyl acetate were added thereto, and the resulting mixture was mixed for 5 minutes to dissolve the precipitates. The resulting solution was left to stand, and then the aqueous phase was removed. Thereafter, saturated sodium hydrogen carbonate solution was added to the obtained organic phase to allow neutralization, followed by confirming that the pH of the aqueous phase in the lower layer, became not less than 9. After extraction of the aqueous phase in the lower layer, demineralized water was added to the obtained organic phase, and the resulting mixture was stirred for 10 minutes. Thereafter, the mixture was left to stand, and the aqueous phase was extracted. Part of the obtained organic phase was removed, and subjected to high-performance liquid chromatography to analyze the amount of bisphenol C produced. As a result, the amount was found to be 40 mol %. The production rate of isopropenyl cresol dimer was 6.2% by area.

Reference Example 7

In a full-jacket type 1.5 L separable flask equipped with a thermometer, a stirrer, and a dropping funnel, 12 g (3.1 mmol) of methanol, 320 g of toluene, 230.0 g (2.1 mol) of ortho-cresol, 51.0 g (0.9 mol) of acetone, and 5.3 g (0.03 mol) of dodecanethiol were added under a nitrogen atmosphere, and the temperature was set to 30° C. In the dropping funnel, 250 g (0.7 mol) of 70% sulfuric acid was added, and it was slowly fed dropwise to the separable flask while the internal temperature was maintained at 30° C. Upon completion of the dropwise addition of sulfuric acid, the reaction liquid had a red-brown color. The reaction liquid was mixed at 30° C. for 1 hour, and the temperature was then increased to 45° C. to allow the reaction to proceed. After completion of the reaction, 175.5 g of demineralized water and 125 g of 28% aqueous sodium hydroxide solution were fed thereto, followed by increasing the temperature to 80° C. After the temperature reached 80° C., the reaction liquid was left to stand to confirm that the precipitates generated during the reaction were dissolved into the organic phase and the aqueous phase. This was followed by extraction of the aqueous phase in the lower layer. Thereafter, saturated sodium hydrogen carbonate solution was added to the obtained organic phase to allow neutralization, followed by confirming that the pH of the aqueous phase in the lower layer, became not less than 9. After extraction of the aqueous phase in the lower layer, demineralized water was added to the obtained organic phase, and the resulting mixture was stirred for 10 minutes. Thereafter, the mixture was left to stand, and the aqueous phase was extracted. Part of the obtained organic phase was removed, and subjected to high-performance liquid chromatography to analyze the amount of bisphenol C produced. As a result, the reaction yield in terms of acetone was found to be 53 mol %. The production rate of isopropenyl cresol dimer was 0.3% by area.

Reference Example 8

In a full-jacket type 1.5 L separable flask equipped with a thermometer, a stirrer, and a dropping funnel, 85 g of methanol, 168 g (1.6 mol) of ortho-cresol, and 30 g (0.5 mol) of acetone were added under a nitrogen atmosphere, and the temperature was set to 10° C. In the dropping funnel, 100 g of 98% sulfuric acid was added, and it was slowly fed dropwise to the separable flask while the internal temperature was maintained at 10° C. Upon completion of the dropwise addition of sulfuric acid, the reaction liquid was a homogeneous solution with a red-brown color. The reaction liquid was mixed as it is at 10° C. for 1 hour, and then 200 g of toluene was added thereto, followed by setting the temperature to 30° C. to allow separation into two phases. Part of the obtained organic phase was removed, and subjected to high-performance liquid chromatography to analyze the amount of bisphenol C produced. As a result, it was found that bisphenol C was present in a trace amount (1 mol %), and that a plurality of by-products was also produced.

For Examples 9 to 11, Comparative Example 5, and Reference Examples 7 and 8, the type of the catalyst, the color tone of the reaction liquid, properties of the reaction liquid, and the reaction yield of bisphenol C, and the like are summarized in Table 3.

monomethyl sulfate solution was slowly sent to the 8 m³ glass-lined reaction vessel, and then acetone was slowly fed thereto such that the internal temperature of the reaction vessel did not exceed 30° C. After the feeding of the acetone, the internal temperature of the reaction vessel was increased to 50° C., and the mixture was mixed for 15 hours to complete the reaction. Thereafter, 985 kg of toluene, 1278 kg of water, and 1160 kg of 28% by weight sodium hydroxide solution were slowly fed thereto such that the internal temperature of the reaction vessel was not more than 50° C. Thereafter, the temperature was increased to 80° C., and the mixture was left to stand, followed by extraction of the aqueous phase in the lower layer. To the obtained organic phase, 599 kg of 1.5% by weight sodium hydrogen carbonate solution was added, and the resulting mixture was mixed, followed by leaving the mixture to stand and then extracting the aqueous phase in the lower layer. As result of slow cooling of the obtained organic phase to 10° C., precipitation of bisphenol C occurred to form a slurry. Using a centrifuge, a filtrate was separated from the slurry to obtain 1627 kg of a wet cake. The wet cake was fed to a full-jacket type 6.8 m³

TABLE 3

| | | Concentration of monomethyl sulfate | Color tone of reaction liquid | Production rate of isopropenyl cresol dimer (% by area) | Properties of reaction liquid | Reaction yield (mol % in terms of acetone) |
|---|---|---|---|---|---|---|
| Example 9 | Monomethyl sulfate (sulfuric acid + methanol) | 30 wt % | Orange | 0.7 | ○ | 85 |
| Example 10 | Monomethyl sulfate (sulfuric acid + methanol) | 10 wt ppm | Orange | 0.24 | ○ | 69 |
| Example 11 | Monomethyl sulfate (sulfuric acid + methanol) | 0.1 wt % | Orange | 0.13 | ○ | 63 |
| Comparative Example 5 | Monomethyl sulfate (sulfuric acid + methanol) | Below detection limit | Red-brown | 6.2 | x | 40 |
| Reference Example 7 | Methanol, dropwise addition of sulfuric acid | ※1 | Red-brown | 0.3 | ○ | 53 |
| Reference Example 8 | Methanol, dropwise addition of sulfuric acid | ※1 | Red-brown | Below detection limit | ○ | ※2 |

※1: Measurement was impossible since dropwise addition of sulfuric acid and analysis of monomethyl sulfate cannot be carried out at the same time.
※2: Bisphenol C was in a trace amount.

From Table 3, it was found that, by using monomethyl sulfate as a catalyst, a bisphenol C having an excellent color tone can be obtained with a high yield while suppressing coloring of the reaction liquid and production of isopropenyl cresol dimer as a by-product, and without solidification of the reaction liquid.

Example 12

To a full-jacket type 1 m³ glass-lined reaction vessel equipped with a thermometer, a stirrer, and a dropper, 566 kg of 88% sulfuric acid was fed, and 255 kg of methanol was fed to the dropper. The methanol was slowly added dropwise to the reaction vessel, to obtain a monomethyl sulfate solution. To a full-jacket type 8 m³ glass-lined reaction vessel equipped with a thermometer, a stirrer, and a drop tank, 530 kg of toluene, 1861 kg of ortho-cresol (17.2 kmol), and 53 kg of dodecyl mercaptan were fed, and 413 kg (7.1 kmol) of acetone was fed to the drop tank. Thereafter, the stainless-steel crystallization tank, and then 2442 kg of toluene was fed thereto. The temperature in the crystallization tank was increased to 80° C., and 551 kg of pure water was added thereto, followed by mixing the resulting mixture. The mixture was then left to stand, and the aqueous phase in the lower layer, was extracted. Further, 552 kg of pure water was added to the crystallization tank, followed by mixing the resulting mixture. The mixture was then left to stand, and the aqueous phase in the lower layer, was extracted. To the organic phase obtained, 27 kg of 0.001% by weight sodium chloride solution was added, and the resulting mixture was cooled to 10° C. As a result, precipitation of bisphenol C occurred to form a slurry. Using a centrifuge, a filtrate was separated from the slurry, and 1537 kg of a wet cake was obtained after sprinkle-washing with 780 kg of toluene. The obtained wet cake was fed to a 6.5 m³ dryer to allow sufficient drying, to obtain 1440 kg (5.6 kmol; yield in terms of acetone, 79 mol %) of a bisphenol. For Examples 9 and 12, the amount of acetone used and the reaction yield of bisphenol C are summarized in Table 4. As a result, it was found that a bisphenol can be similarly produced also in cases where an increased amount of acetone is used.

TABLE 4

Amount of acetone used and isolation yield of bisphenol C

|  | Amount of acetone used | Isolation yield of bisphenol C (mol % in terms of acetone) |
|---|---|---|
| Example 9 | 57 g | 72 |
| Example 12 | 413 kg | 79 |

Example 13

In a full-jacket type 200 mL separable flask equipped with a thermometer, a stirrer, and a 100 mL dropping funnel, 6.9 g (0.2 mol) of methanol was added under a nitrogen atmosphere, and then 15.4 g (0.1 mol) of 92% by weight sulfuric acid was slowly added thereto to provide a solution in which monomethyl sulfate was produced. Thereafter, 14.4 g of toluene, 50.6 g (0.5 mol) of ortho-cresol, and 1.4 g (0.01 mol) of dodecanethiol were added thereto, followed by setting the temperature in the separable flask to 40° C. In the dropping funnel, 11.2 g (0.20 mol) of acetone was added, and it was slowly fed dropwise to the separable flask for 30 minutes. After completion of the dropwise addition of acetone, the reaction was allowed to proceed at 40° C. for 5 hours. After completion of the reaction, 50.0 g of toluene and 50.0 g of demineralized water were fed, and the temperature was increased to 80° C. After the temperature reached 80° C., the reaction liquid was left to stand to confirm that the precipitates generated during the reaction were dissolved into the organic phase and the aqueous phase. This was followed by extraction of the aqueous phase in the lower layer. Thereafter, saturated sodium hydrogen carbonate solution was added to the obtained organic phase to allow neutralization, followed by confirming that the pH of the aqueous phase in the lower layer, became not less than 9. After extraction of the aqueous phase in the lower layer, demineralized water was added to the obtained organic phase, and the resulting mixture was stirred for 10 minutes. Thereafter, the mixture was left to stand, and the aqueous phase was extracted. Part of the obtained organic phase was removed, and subjected to high-performance liquid chromatography to analyze the amount of bisphenol C produced. As a result, the reaction yield in terms of acetone was found to be 89 mol %.

Example 14

In a full-jacket type 1 L separable flask equipped with a thermometer, a stirrer, and a 100 mL dropping funnel, 21.2 g (0.7 mol) of methanol was added under a nitrogen atmosphere, and then 46.5 g (0.4 mol) of 92% by weight sulfuric acid was slowly added thereto to provide a solution in which monomethyl sulfate was produced. Thereafter, 122.4 g of ortho-xylene, 137.7 g (1.3 mol) of ortho-cresol, and 4.4 g (0.02 mol) of dodecanethiol were added thereto, followed by setting the temperature in the separable flask to 40° C. In the dropping funnel, 34.3 g (0.6 mol) of acetone was added, and it was slowly fed dropwise to the separable flask for 30 minutes. After completion of the dropwise addition of acetone, the reaction was allowed to proceed at 40° C. for 2 hours. After completion of the reaction, 100.0 g of ortho-xylene and 100.0 g of demineralized water were fed, and the temperature was increased to 80° C. After the temperature reached 80° C., the reaction liquid was left to stand to confirm that the precipitates generated during the reaction were dissolved into the organic phase and the aqueous phase. This was followed by extraction of the aqueous phase in the lower layer. Thereafter, saturated sodium hydrogen carbonate solution was added to the obtained organic phase to allow neutralization, followed by confirming that the pH of the aqueous phase in the lower layer, became not less than 9. After extraction of the aqueous phase in the lower layer, demineralized water was added to the obtained organic phase, and the resulting mixture was stirred for 10 minutes. Thereafter, the mixture was left to stand, and the aqueous phase was extracted. Part of the obtained organic phase was removed, and subjected to high-performance liquid chromatography to analyze the amount of bisphenol C produced. As a result, the reaction yield in terms of acetone was found to be 88 mol %.

Example 15

The same operation as in Example 14 was carried out except that 137.4 g of para-xylene was added instead of 122.4 g of ortho-xylene to the separable flask, and that, after completion of the reaction, 100 g of para-xylene was added instead of 100 g of ortho-xylene. Part of the obtained organic phase was removed, and subjected to high-performance liquid chromatography to analyze the amount of bisphenol C produced. As a result, the reaction yield in terms of acetone was found to be 91 mol %.

Example 16

The same operation as in Example 14 was carried out except that 122.4 g of xylene was added instead of 122.4 g of ortho-xylene to the separable flask, and that, after completion of the reaction, 100 g of xylene was added instead of 100 g of ortho-xylene. Part of the obtained organic phase was removed, and subjected to high-performance liquid chromatography to analyze the amount of bisphenol C produced. As a result, the reaction yield in terms of acetone was found to be 88 mol %.

Example 17

The same operation as in Example 14 was carried out except that 122.2 g of mesitylene was added instead of 122.4 g of ortho-xylene to the separable flask, and that, after completion of the reaction, 100 g of mesitylene was added instead of 100 g of ortho-xylene. Part of the obtained organic phase was removed, and subjected to high-performance liquid chromatography to analyze the amount of bisphenol C produced. As a result, the reaction yield in terms of acetone was found to be 85 mol %.

Example 18

The same operation as in Example 14 was carried out except that 65.0 g of chlorobenzene was added instead of 122.4 g of ortho-xylene to the separable flask, and that, after completion of the reaction, 100 g of chlorobenzene was added instead of 100 g of ortho-xylene. Part of the obtained organic phase was removed, and subjected to high-performance liquid chromatography to analyze the amount of bisphenol C produced. As a result, the reaction yield in terms of acetone was found to be 60 mol %.

For Examples 13 to 18, the type of the solvent and the reaction yield are summarized in Table 5. As a result, it became clear that a bisphenol C can be obtained with a high yield even with different types of solvents.

TABLE 5

Type of solvent and reaction yield of bisphenol C

| | Type of solvent | Reaction yield of bisphenol C (mol % in terms of acetone) |
|---|---|---|
| Example 13 | Toluene | 89 |
| Example 14 | Ortho-xylene | 88 |
| Example 15 | Para-xylene | 91 |
| Example 16 | Xylene | 88 |
| Example 17 | Mesitylene | 85 |
| Example 18 | Chlorobenzene | 60 |

Example 19

In a full-jacket type 1 L separable flask equipped with a thermometer, a stirrer, and a 100 mL dropping funnel, 26.1 g (0.4 mol) of isopropyl alcohol was added under a nitrogen atmosphere, and then 58.3 g (0.5 mol) of 90% by weight sulfuric acid was slowly added thereto. Thereafter, 54.5 g of toluene, 191.5 g (1.8 mol) of ortho-cresol, and 5.5 g (0.03 mol) of dodecanethiol were added thereto, followed by setting the temperature in the separable flask to 40° C. In the dropping funnel, 42.5 g (0.7 mol) of acetone was placed, and it was slowly fed dropwise to the separable flask for 30 minutes. After completion of the dropwise addition of acetone, the reaction was allowed to proceed at 40° C. for 2 hours. After completion of the reaction, 100.0 g of toluene and 100.0 g of demineralized water were fed, and the temperature was increased to 80° C. After the temperature reached 80° C., the reaction liquid was left to stand to confirm that the precipitates generated during the reaction were dissolved into the organic phase and the aqueous phase. This was followed by extraction of the aqueous phase in the lower layer. Thereafter, saturated sodium hydrogen carbonate solution was added to the obtained organic phase to allow neutralization, followed by confirming that the pH of the aqueous phase in the lower layer, became not less than 9. After extraction of the aqueous phase in the lower layer, demineralized water was added to the obtained organic phase, and the resulting mixture was stirred for 10 minutes. Thereafter, the mixture was left to stand, and the aqueous phase was extracted. Part of the obtained organic phase was removed, and subjected to high-performance liquid chromatography to analyze the amount of bisphenol C produced. As a result, the reaction yield in terms of acetone was found to be 84 mol %.

Example 20

The same operation as in Example 19 was carried out except that 26.2 g (0.2 mol) of 1-octanol was fed instead of 26.1 g of isopropyl alcohol. Part of the obtained organic phase was removed, and subjected to high-performance liquid chromatography to analyze the amount of bisphenol C produced. As a result, the reaction yield in terms of acetone was found to be 82 mol %.

Example 21

The same operation as in Example 19 was carried out except that 18.4 g (0.3 mol) of ethylene glycol was fed instead of 26.1 g of isopropyl alcohol. Part of the obtained organic phase was removed, and subjected to high-performance liquid chromatography to analyze the amount of bisphenol C produced. As a result, the reaction yield in terms of acetone was found to be 75 mol %.

For Example 13 and Examples 19 to 21, the type of the aliphatic alcohol and the reaction yield are summarized in Table 6. As a result, it became clear that a bisphenol C can be obtained with a high yield even with different types of aliphatic alcohols.

TABLE 6

Type of aliphatic alcohol and reaction yield of bisphenol C

| | Type of aliphatic alcohol | Reaction yield of bisphenol C (mol % in terms of acetone) |
|---|---|---|
| Example 13 | Methanol | 89 |
| Example 19 | Isopropyl alcohol | 84 |
| Example 20 | 1-Octanol | 82 |
| Example 21 | Ethylene glycol | 75 |

Example 22

The same operation as in Example 19 was carried out except that 2.9 g (0.01 mol) of 3-mercaptopropionic acid was fed instead of 5.5 g of dodecanethiol, and that 26.3 g (0.8 mol) of methanol was fed instead of 26.1 g of isopropyl alcohol. Part of the obtained organic phase was removed, and subjected to high-performance liquid chromatography to analyze the amount of bisphenol C produced. As a result, the reaction yield in terms of acetone was found to be 98 mol %.

Example 23

The same operation as in Example 19 was carried out except that 2.9 g (0.01 mol) of 3-mercaptopropionic acid was fed instead of 5.5 g of dodecanethiol, and that 18.4 g (0.3 mol) of ethylene glycol was fed instead of 26.1 g of isopropyl alcohol. Part of the obtained organic phase was removed, and subjected to high-performance liquid chromatography to analyze the amount of bisphenol C produced. As a result, the reaction yield in terms of acetone was found to be 89 mol %.

For Example 13 and Examples 21 to 23, the type of the aliphatic alcohol, the type of the thiol, and the reaction yield are summarized in Table 7. As a result, it became clear that a bisphenol C can be obtained with a high yield even with different types of aliphatic alcohols and thiols.

TABLE 7

Type of aliphatic alcohol, type of thiol, and reaction yield of bisphenol C

| | Type of aliphatic alcohol | Type of thiol | Reaction yield of bisphenol C (mol % in terms of acetone) |
|---|---|---|---|
| Example 13 | Methanol | Dodecyl mercaptan | 89 |
| Example 21 | Ethylene glycol | Dodecyl mercaptan | 75 |
| Example 22 | Methanol | 3-Mercaptopropionic acid | 98 |
| Example 23 | Ethylene glycol | 3-Mercaptopropionic acid | 89 |

Example 24

In a full-jacket type 1 L separable flask equipped with a thermometer, a stirrer, and a 100 mL dropping funnel, 1.7 g (0.1 mol) of methanol was added under a nitrogen atmosphere, and then 33.0 g (0.3 mol) of 92% by weight sulfuric acid was slowly added thereto to provide a solution in which monomethyl sulfate was produced. Thereafter, 18 g of toluene, 63.0 g (0.7 mol) of phenol, and 1.7 g (0.05 mol) of dodecanethiol were added thereto, followed by setting the temperature in the separable flask to 40° C. In the dropping funnel, 16.0 g (0.3 mol) of acetone was placed, and it was slowly fed dropwise to the separable flask for 30 minutes. After completion of the dropwise addition of acetone, the reaction was allowed to proceed at 40° C. for 2 hours. After completion of the reaction, 100.0 g of ethyl acetate and 100.0 g of demineralized water were fed, and the resulting mixture was mixed. Thereafter, the mixture was left to stand, and the aqueous phase in the lower layer, was extracted. Thereafter, saturated sodium hydrogen carbonate solution was added to the obtained organic phase to allow neutralization, followed by confirming that the pH of the aqueous phase in the lower layer, became not less than 9. After extraction of the aqueous phase in the lower layer, demineralized water was added to the obtained organic phase, and the resulting mixture was stirred for 10 minutes. Thereafter, the mixture was left to stand, and the aqueous phase was extracted. Part of the obtained organic phase was removed and subjected to analysis by high-performance liquid chromatography. As a result, production of 2,2-bis(4-hydroxyphenyl) propane (hereinafter referred to as bisphenol A) was found. Its amount was 73.2% by area.

Example 25

In a full-jacket type 1 L separable flask equipped with a thermometer, a stirrer, and a 100 mL dropping funnel, 8.7 g (0.3 mol) of methanol was added under a nitrogen atmosphere, and then 19.4 g (0.2 mol) of 90% by weight sulfuric acid was slowly added thereto to provide a solution in which monomethyl sulfate was produced. Thereafter, 18.1 g of toluene, 63.8 g (0.7 mol) of phenol, and 1.8 g (0.01 mol) of dodecanethiol were added thereto, followed by setting the temperature in the separable flask to 40° C. In the dropping funnel, 44.9 g (0.2 mol) of dodecanal was placed, and it was slowly fed dropwise to the separable flask for 30 minutes. After completion of the dropwise addition of dodecanal, the reaction was allowed to proceed at 40° C. for 2 hours. After completion of the reaction, 100.0 g of ethyl acetate and 100.0 g of demineralized water were fed, and the resulting mixture was mixed. Thereafter, the mixture was left to stand, and the aqueous phase in the lower layer, was extracted. Thereafter, saturated sodium hydrogen carbonate solution was added to the obtained organic phase to allow neutralization, followed by confirming that the pH of the aqueous phase in the lower layer, became not less than 9. After extraction of the aqueous phase in the lower layer, demineralized water was added to the obtained organic phase, and the resulting mixture was stirred for 10 minutes. Thereafter, the mixture was left to stand, and the aqueous phase was extracted. Part of the obtained organic phase was removed and subjected to analysis by high-performance liquid chromatography. As a result, production of 1,1-bis(4-hydroxyphenyl) dodecane was found. The obtained organic phase was transferred to a 1 L recovery flask, and toluene, ethyl acetate, and phenol were removed by distillation using an evaporator. To the residual liquid, heptane and isopropyl alcohol were fed to allow crystallization. The resulting slurry was subjected to solid-liquid separation using a vacuum filter equipped with a glass filter, to obtain a white solid. The white solid was transferred to a 500 mL recovery flask, and then dried using an evaporator, to obtain 30.5 g (0.1 mol; yield, 35 mol %) of 1,1-bis(4-hydroxyphenyl) dodecane.

Example 26

In a full-jacket type 1 L separable flask equipped with a thermometer, a stirrer, and a 100 mL dropping funnel, 8.7 g (0.3 mol) of methanol was added under a nitrogen atmosphere, and then 19.4 g (0.2 mol) of 90% by weight sulfuric acid was slowly added thereto to provide a solution in which monomethyl sulfate was produced. Thereafter, 18.2 g of toluene, 63.8 g (0.6 mol) of ortho-cresol, and 1.8 g (0.01 mol) of dodecanethiol were added thereto, followed by setting the temperature in the separable flask to 40° C. In the dropping funnel, 44.9 g (0.2 mol) of dodecanal was added, and it was slowly fed dropwise to the separable flask for 30 minutes. After completion of the dropwise addition of dodecanal, the reaction was allowed to proceed at 40° C. for 2 hours. After completion of the reaction, 100.0 g of ethyl acetate and 100.0 g of demineralized water were fed, and the resulting mixture was mixed. Thereafter, the mixture was left to stand, and the aqueous phase in the lower layer, was extracted. Thereafter, saturated sodium hydrogen carbonate solution was added to the obtained organic phase to allow neutralization, followed by confirming that the pH of the aqueous phase in the lower layer, became not less than 9. After extraction of the aqueous phase in the lower layer, demineralized water was added to the obtained organic phase, and the resulting mixture was stirred for 10 minutes. Thereafter, the mixture was left to stand, and the aqueous phase was extracted. Part of the obtained organic phase was removed, and subjected to measurement using a high-performance liquid chromatograph-mass spectrometer. As a result, a mass number of 381 ($M^+$-1) was found in the negative mode, indicating production of 1,1-bis(4-hydroxy-3-methylphenyl) dodecane. According to high-performance liquid chromatography, the 1,1-bis(4-hydroxy-3-methylphenyl) dodecane was found to have been produced at 60.7% by area.

Example 27

In a full-jacket type 1 L, separable flask equipped with a thermometer, a stirrer, and 100 mL, 26 g (0.8 mol) of methanol was added under a nitrogen atmosphere, and then 58.5 g (0.5 mol) of 90% by weight sulfuric acid was slowly added thereto to provide a solution in which monomethyl sulfate was produced. Thereafter, 60 g of toluene, 197.0 g (1.8 mol) of ortho-cresol, and 5.5 g (0.03 mol) of dodecanethiol were added thereto, followed by setting the temperature in the separable flask to 50° C. Subsequently, 136 g (0.8 mol) of fluorenone was placed therein, and slowly fed dropwise to the separable flask for 30 minutes. Thereafter, the reaction was allowed to proceed at 50° C. for 2 hours. After completion of the reaction, 100.0 g of ethyl acetate and 100.0 g of demineralized water were fed, and the resulting mixture was mixed. Thereafter, the mixture was left to stand, and the aqueous phase in the lower layer, was extracted. Thereafter, saturated sodium hydrogen carbonate solution was added to the obtained organic phase to allow neutralization, followed by confirming that the pH of the aqueous phase in the lower layer, became not less than 9. After extraction of the aqueous phase in the lower layer, demineralized water was added to the obtained organic phase, and the resulting mixture was stirred for 10 minutes. Thereafter, the mixture was left to stand, and the aqueous phase was extracted. Part of the obtained organic phase was removed and subjected to measurement by high-performance liquid chromatography. As a result, production of 9,9-bis(4-hydroxy-3-methylphenyl) fluorene was found. Its production rate was 85.6% by area.

Example 28

In a full-jacket type 1 L separable flask equipped with a thermometer, a stirrer, and a 100 mL dropping funnel, 26.2 g (0.8 mol) of methanol was added under a nitrogen atmosphere, and then 58.5 g (0.6 mol) of 92% by weight sulfuric acid was slowly added thereto to provide a solution in which monomethyl sulfate was produced. Thereafter, 58.5 g of toluene, 192 g (1.8 mol) of ortho-cresol, and 5.5 g (0.03 mol) of dodecanethiol were added thereto, followed by setting the temperature in the separable flask to 50° C. In the dropping funnel, 71.8 g (0.7 mol) of cyclohexanone was added, and it was slowly fed dropwise to the separable flask for 30 minutes. After completion of the dropwise addition of cyclohexanone, the reaction was allowed to proceed at 50° C. for 5 hours. After completion of the reaction, 100.0 g of ethyl acetate and 100.0 g of demineralized water were fed, and the resulting mixture was mixed. Thereafter, the mixture was left to stand, and the aqueous phase in the lower layer, was extracted. Thereafter, saturated sodium hydrogen carbonate solution was added to the obtained organic phase to allow neutralization, followed by confirming that the pH of the aqueous phase in the lower layer, became not less than 9. After extraction of the aqueous phase in the lower layer, demineralized water was added to the obtained organic phase, and the resulting mixture was stirred for 10 minutes. Thereafter, the mixture was left to stand, and the aqueous phase was extracted. Part of the obtained organic phase was removed, and subjected to measurement using a high-performance liquid chromatograph-mass spectrometer. As a result, a mass number of 295 (M %-1) was found in the negative mode, indicating production of 1,1-bis(4-hydroxy-3-methylphenyl) cyclohexane. As a result of analysis using high-performance liquid chromatography, the production rate of 1,1-bis(4-hydroxy-3-methylphenyl) cyclohexane was found to be 70.8% by area.

Example 29

In a full-jacket type 1 L separable flask equipped with a thermometer, a stirrer, and a 100 mL dropping funnel, 26.2 g (0.8 mol) of methanol was added under a nitrogen atmosphere, and then 58.5 g (0.6 mol) of 92% by weight sulfuric acid was slowly added thereto to provide a solution in which monomethyl sulfate was produced. Thereafter, 58.5 g of toluene, 191 g (1.8 mol) of ortho-cresol, and 5.5 g (0.03 mol) of dodecanethiol were added thereto, followed by setting the temperature in the separable flask to 50° C. In the dropping funnel, 42.5 g (0.4 mol) of cycloheptanone was placed, and it was slowly fed dropwise to the separable flask for 30 minutes. After completion of the dropwise addition of cycloheptanone, the reaction was allowed to proceed at 50° C. for 5 hours. After completion of the reaction, 100.0 g of ethyl acetate and 100.0 g of demineralized water were fed, and the resulting mixture was mixed. Thereafter, the mixture was left to stand, and the aqueous phase in the lower layer, was extracted. Thereafter, saturated sodium hydrogen carbonate solution was added to the obtained organic phase to allow neutralization, followed by confirming that the pH of the aqueous phase in the lower layer, became not less than 9. After extraction of the aqueous phase in the lower layer, demineralized water was added to the obtained organic phase, and the resulting mixture was stirred for 10 minutes. Thereafter, the mixture was left to stand, and the aqueous phase was extracted. Part of the obtained organic phase was removed, and subjected to measurement using a high-performance liquid chromatograph-mass spectrometer. As a result, a mass number of 309 ($M^+$-1) was found in the negative mode, indicating production of 1,1-bis(4-hydroxy-3-methylphenyl) cycloheptane. As a result of analysis using high-performance liquid chromatography, the production rate of 1,1-bis(4-hydroxy-3-methylphenyl) cycloheptane was found to be 25.9% by area.

Example 30

In a full-jacket type 1 L separable flask equipped with a thermometer, a stirrer, and a 100 mL dropping funnel, 26.2 g (0.8 mol) of methanol was added under a nitrogen atmosphere, and then 58.5 g (0.6 mol) of 92% by weight sulfuric acid was slowly added thereto to provide a solution in which monomethyl sulfate was produced. Thereafter, 58.5 g of toluene, 191.5 g (1.8 mol) of ortho-cresol, and 5.5 g (0.03 mol) of dodecanethiol were added thereto, followed by setting the temperature in the separable flask to 50° C. In the dropping funnel, 52.7 g (0.7 mol) of methyl ethyl ketone was added, and it was slowly fed dropwise to the separable flask for 30 minutes. After completion of the dropwise addition of methyl ethyl ketone, the reaction was allowed to proceed at 50° C. for 5 hours. After completion of the reaction, 100.0 g of ethyl acetate and 100.0 g of demineralized water were fed, and the resulting mixture was mixed. Thereafter, the mixture was left to stand, and the aqueous phase in the lower layer, was extracted. Thereafter, saturated sodium hydrogen carbonate solution was added to the obtained organic phase to allow neutralization, followed by confirming that the pH of the aqueous phase in the lower layer, became not less than 9. After extraction of the aqueous phase in the lower layer, demineralized water was added to the obtained organic phase, and the resulting mixture was stirred for 10 minutes. Thereafter, the mixture was left to stand, and the aqueous phase was extracted. Part of the obtained organic phase was removed, and subjected to measurement using a high-performance liquid chromatograph-mass spectrometer. As a result, a mass number of 269 ($M^+$-1) was found in the negative mode, indicating production of 2,2-bis(4-hydroxy-3-methylphenyl) butane. As a result of analysis using high-performance liquid chromatography, the production rate of 2,2-bis(4-hydroxy-3-methylphenyl) butane was found to be 47.6% by area.

Example 31

In a full-jacket type 1 L separable flask equipped with a thermometer, a stirrer, and a 100 mL dropping funnel, 26.2 g (0.8 mol) of methanol was added under a nitrogen atmosphere, and then 58.5 g (0.6 mol) of 92% by weight sulfuric acid was slowly added thereto to provide a solution in which monomethyl sulfate was produced. Thereafter, 58.5 g of toluene, 191.5 g (1.8 mol) of ortho-cresol, and 5.5 g (0.03 mol) of dodecanethiol were added thereto, followed by setting the temperature in the separable flask to 50° C. In the dropping funnel, 73.2 g (0.7 mol) of methyl isobutyl ketone was added, and it was slowly fed dropwise to the separable flask for 30 minutes. After completion of the dropwise addition of methyl isobutyl ketone, the reaction was allowed to proceed at 50° C. for 5 hours. After completion of the reaction, 100.0 g of ethyl acetate and 100.0 g of demineralized water were fed, and the resulting mixture was mixed. Thereafter, the mixture was left to stand, and the aqueous phase in the lower layer, was extracted. Thereafter, saturated sodium hydrogen carbonate solution was added to the obtained organic phase to allow neutralization, followed by confirming that the pH of the aqueous phase in the lower layer, became not less than 9. After extraction of the aqueous phase in the lower layer, demineralized water was added to the obtained organic phase, and the resulting mixture was stirred for 10 minutes. Thereafter, the mixture was left to stand, and the aqueous phase was extracted. Part of the obtained organic phase was removed, and subjected to measurement using a high-performance liquid chromatograph-mass spectrometer. As a result, a mass number of 297 ($M'$-1) was found in the negative mode, indicating production of 2,2-bis(4-hydroxy-3-methylphenyl)-4-methylpentane. As a result of analysis using high-performance liquid chromatography, the production rate of 2,2-bis(4-hydroxy-3-methylphenyl)-4-methylpentane was found to be 65.7% by area.

Example 32

In a full-jacket type 1 L separable flask equipped with a thermometer, a stirrer, and a 100 mL dropping funnel, 26.2 g (0.8 mol) of methanol was added under a nitrogen atmosphere, and then 58.5 g (0.6 mol) of 92% by weight sulfuric acid was slowly added thereto to provide a solution in which monomethyl sulfate was produced. Thereafter, 18 g of toluene, 72 g (0.6 mol) of 2,6-xylenol, and 1.8 g (0.01 mol) of dodecanethiol were added thereto, followed by setting the temperature in the separable flask to 40° C. In the dropping funnel, 14.6 g (0.3 mol) of acetone was added, and it was slowly fed dropwise to the separable flask for 30 minutes. After completion of the dropwise addition of acetone, the reaction was allowed to proceed at 40° C. for 2 hours. After completion of the reaction, 100.0 g of ethyl acetate and 100.0 g of demineralized water were fed, and the resulting mixture was mixed. Thereafter, the mixture was left to stand, and the aqueous phase in the lower layer, was extracted. Thereafter, saturated sodium hydrogen carbonate solution was added to the obtained organic phase to allow neutralization, followed by confirming that the pH of the aqueous phase in the lower layer, became not less than 9. After extraction of the aqueous phase in the lower layer, demineralized water was added to the obtained organic phase, and the resulting mixture was stirred for 10 minutes. Thereafter, the mixture was left to stand, and the aqueous phase was extracted. Part of the obtained organic phase was removed and subjected to measurement by high-performance liquid chromatography. As a result, production of 2,2-bis(4-hydroxy-3,5-dimethylphenyl) propane was found. The production rate of the 2,2-bis(4-hydroxy-3,5-dimethylphenyl) propane was 41.9% by area.

Example 33

In a full-jacket type 1 L separable flask equipped with a thermometer, a stirrer, and a 100 mL dropping funnel, 5.0 g (0.2 mol) of methanol was added under a nitrogen atmosphere, and then 100 g (0.9 mol) of 92% by weight sulfuric acid was slowly added thereto to provide a solution in which monomethyl sulfate was produced. Thereafter, 54.3 g of toluene, 152 g (1.6 mol) of phenol, and 5.5 g (0.03 mol) of dodecanethiol were added thereto, followed by setting the temperature in the separable flask to 50° C. In the dropping funnel, 81 g (0.6 mol) of 3,3,5-trimethylcyclohexanone was added, and it was slowly fed dropwise to the separable flask for 30 minutes. After completion of the dropwise addition of 3,3,5-trimethylcyclohexanone, the reaction was allowed to proceed at 50° C. for 2 hours. After completion of the reaction, 100.0 g of ethyl acetate and 100.0 g of demineralized water were fed, and the resulting mixture was mixed. Thereafter, the mixture was left to stand, and the aqueous phase in the lower layer, was extracted. Thereafter, saturated sodium hydrogen carbonate solution was added to the obtained organic phase to allow neutralization, followed by confirming that the pH of the aqueous phase in the lower layer, became not less than 9. After extraction of the aqueous phase in the lower layer, demineralized water was added to the obtained organic phase, and the resulting mixture was stirred for 10 minutes. Thereafter, the mixture was left to stand, and the aqueous phase was extracted. Part of the obtained organic phase was removed, and subjected to measurement using a high-performance liquid chromatograph-mass spectrometer. As a result, a mass number of 309 ($M^+$-1) was found in the negative mode, indicating production of 1,1-bis(4-hydroxyphenyl)-3,3,5-trimethylcyclohexane. As a result of analysis using high-performance liquid chromatography, the production rate of 1,1-bis(4-hydroxyphenyl)-3,3,5-trimethylcyclohexane was found to be 62.5% by area.

Example 34

In a full-jacket type 1 L separable flask equipped with a thermometer, a stirrer, and a 100 mL dropping funnel, 4 g (0.1 mol) of methanol was added under a nitrogen atmosphere, and then 84 g (0.7 mol) of 85% by weight sulfuric acid was slowly added thereto to provide a solution in which monomethyl sulfate was produced. Thereafter, 54 g of toluene, 151 g (1.4 mol) of ortho-cresol, and 5.5 g (0.03 mol) of dodecanethiol were added thereto, followed by setting the temperature in the separable flask to 40° C. In the dropping funnel, 70 g (0.6 mol) of acetophenone was added, and it was slowly fed dropwise to the separable flask for 30 minutes. After completion of the dropwise addition of acetophenone, the reaction was allowed to proceed at 40° C. for 2 hours. After completion of the reaction, 100.0 g of ethyl acetate and 100.0 g of demineralized water were fed, and the resulting mixture was mixed. Thereafter, the mixture was left to stand, and the aqueous phase in the lower layer, was extracted. Thereafter, saturated sodium hydrogen carbonate solution was added to the obtained organic phase to allow neutralization, followed by confirming that the pH of the aqueous phase in the lower layer, became not less than 9. After extraction of the aqueous phase in the lower layer, demineralized water was added to the obtained organic phase, and the resulting mixture was stirred for 10 minutes. Thereafter, the mixture was left to stand, and the aqueous phase was extracted. Part of the obtained organic phase was removed, and subjected to measurement using a high-performance liquid chromatograph-mass spectrometer. As a result, a mass number of 317 ($M^+$-1) was found in the negative mode, indicating production of 1,1-bis(4-hydroxy-3,5-dimethylphenyl)-1-phenylethane. As a result of analysis using high-performance liquid chromatography, the production rate of 1,1-bis(4-hydroxy-3,5-dimethylphenyl)-1-phenylethane was found to be 48.2% by area.

Example 35

In a full-jacket type 1 L separable flask equipped with a thermometer, a stirrer, and a 100 mL dropping funnel, 18 g (0.6 mol) of methanol was added under a nitrogen atmosphere, and then 25.8 g (0.2 mol) of 85% by weight sulfuric acid was slowly added thereto to provide a solution in which monomethyl sulfate was produced. Thereafter, 24 g of toluene, 75 g (0.4 mol) of 2-phenylphenol, and 2.4 g (0.01 mol) of dodecanethiol were added thereto, followed by setting the temperature in the separable flask to 40° C. In the dropping funnel, 10.5 g (0.2 mol) of acetone was added, and it was slowly fed dropwise to the separable flask for 30 minutes. After completion of the dropwise addition of acetone, the reaction was allowed to proceed at 40° C. for 2 hours. After completion of the reaction, 100.0 g of ethyl acetate and 100.0 g of demineralized water were fed, and the resulting mixture was mixed. Thereafter, the mixture was left to stand, and the aqueous phase in the lower layer, was extracted. Thereafter, saturated sodium hydrogen carbonate solution was added to the obtained organic phase to allow neutralization, followed by confirming that the pH of the aqueous phase in the lower layer, became not less than 9. After extraction of the aqueous phase in the lower layer, demineralized water was added to the obtained organic phase, and the resulting mixture was stirred for 10 minutes. Thereafter, the mixture was left to stand, and the aqueous phase was extracted. Part of the obtained organic phase was removed, and subjected to measurement using a high-performance liquid chromatograph-mass spectrometer. As a result, a mass number of 379 ($M^+$-1) was found in the negative mode, indicating production of 2,2-bis(4-hydroxy-3-phenylphenyl) propane. As a result of analysis using high-performance liquid chromatography, the production rate of 2,2-bis(4-hydroxy-3-phenylphenyl) propane was found to be 9.0% by area.

Example 36

In a full-jacket type 1 L separable flask equipped with a thermometer, a stirrer, and a 100 mL dropping funnel, 9 g (0.3 mol) of methanol was added under a nitrogen atmosphere, and then 22 g (0.2 mol) of 85% by weight sulfuric acid was slowly added thereto to provide a solution in which monomethyl sulfate was produced. Thereafter, 24 g of toluene, 50 g (0.3 mol) of 2-cyclohexylphenol, and 2.4 g (0.01 mol) of dodecanethiol were added thereto, followed by setting the temperature in the separable flask to 40° C. In the dropping funnel, 9 g (0.2 mol) of acetone was added, and it was slowly fed dropwise to the separable flask for 30 minutes. After completion of the dropwise addition of acetone, the reaction was allowed to proceed at 40° C. for 2 hours. After completion of the reaction, 100.0 g of ethyl acetate and 100.0 g of demineralized water were fed, and the resulting mixture was mixed. Thereafter, the mixture was left to stand, and the aqueous phase in the lower layer, was extracted. Thereafter, saturated sodium hydrogen carbonate solution was added to the obtained organic phase to allow neutralization, followed by confirming that the pH of the aqueous phase in the lower layer, became not less than 9. After extraction of the aqueous phase in the lower layer, demineralized water was added to the obtained organic phase, and the resulting mixture was stirred for 10 minutes. Thereafter, the mixture was left to stand, and the aqueous phase was extracted. Part of the obtained organic phase was removed, and subjected to measurement using a high-performance liquid chromatograph-mass spectrometer. As a result, a mass number of 391 ($M^+$-1) was found in the negative mode, indicating production of 2,2-bis(4-hydroxy-3-cyclohexylphenyl) propane. As a result of analysis using high-performance liquid chromatography, the production rate of 2,2-bis(4-hydroxy-3-cyclohexylphenyl) propane was found to be 22.9% by area.

Example 37

In a full-jacket type 1 L separable flask equipped with a thermometer, a stirrer, and a 100 mL dropping funnel, 1.1 g (0.03 mol) of methanol was added under a nitrogen atmosphere, and then 25.8 g (0.2 mol) of 85% by weight sulfuric acid was slowly added thereto to provide a solution in which monomethyl sulfate was produced. Thereafter, 7.5 g of toluene, 50 g (0.3 mol) of 2-benzylphenol, and 2.7 g (0.01 mol) of dodecanethiol were added thereto, followed by setting the temperature in the separable flask to 40° C. In the dropping funnel, 7.7 g (0.1 mol) of acetone was added, and it was slowly fed dropwise to the separable flask for 30 minutes. After completion of the dropwise addition of acetone, the reaction was allowed to proceed at 40° C. for 2 hours. After completion of the reaction, 100.0 g of ethyl acetate and 100.0 g of demineralized water were fed, and the resulting mixture was mixed. Thereafter, the mixture was left to stand, and the aqueous phase in the lower layer, was extracted. Thereafter, saturated sodium hydrogen carbonate solution was added to the obtained organic phase to allow neutralization, followed by confirming that the pH of the aqueous phase in the lower layer, became not less than 9. After extraction of the aqueous phase in the lower layer, demineralized water was added to the obtained organic phase, and the resulting mixture was stirred for 10 minutes. Thereafter, the mixture was left to stand, and the aqueous phase was extracted. Part of the obtained organic phase was removed, and subjected to measurement using a high-performance liquid chromatograph-mass spectrometer. As a result, a mass number of 407 ($M^+$-1) was found in the negative mode, indicating production of 2,2-bis(4-hydroxy-3-benzylphenyl) propane. As a result of analysis using high-performance liquid chromatography, the production rate of 2,2-bis(4-hydroxy-3-benzylphenyl) propane was found to be 60.0% by area.

Example 38

In a full-jacket type 1 L separable flask equipped with a thermometer, a stirrer, and a 100 mL dropping funnel, 41.6 g (1.3 mol) of methanol was added under a nitrogen atmosphere, and then 100 g (0.8 mol) of 80% by weight sulfuric acid was slowly added thereto to provide a solution in which monomethyl sulfate was produced. Thereafter, 54.3 g of toluene, 130 g (1.4 mol) of phenol, and 5.5 g (0.03 mol) of dodecanethiol were added thereto, followed by setting the temperature in the separable flask to 30° C. In the dropping funnel, 73 g (0.5 mol) of 2-ethylhexanal was added, and it was slowly fed dropwise to the separable flask for 30 minutes. After completion of the dropwise addition of 2-ethylhexanal, the reaction was allowed to proceed at 30° C. for 2 hours. After completion of the reaction, 100.0 g of ethyl acetate and 100.0 g of demineralized water were fed, and the resulting mixture was mixed. Thereafter, the mixture was left to stand, and the aqueous phase in the lower layer, was extracted. Thereafter, saturated sodium hydrogen carbonate solution was added to the obtained organic phase to allow neutralization, followed by confirming that the pH of the aqueous phase in the lower layer, became not less than 9. After extraction of the aqueous phase in the lower layer, demineralized water was added to the obtained organic phase, and the resulting mixture was stirred for 10 minutes. Thereafter, the mixture was left to stand, and the aqueous phase was extracted. Part of the obtained organic phase was removed, and subjected to measurement using a high-performance liquid chromatograph-mass spectrometer. As a result, a mass number of 297 ($M^+$-1) was found in the negative mode, indicating production of 1,1-bis(4-hydroxyphenyl)-2-ethylhexane. As a result of analysis using high-performance liquid chromatography, the production rate of 1,1-bis(4-hydroxyphenyl)-2-ethylhexane was found to be 52.4% by area.

Example 39

In a full-jacket type 1 L separable flask equipped with a thermometer, a stirrer, and a 100 mL dropping funnel, 41.6 g (1.3 mol) of methanol was added under a nitrogen atmosphere, and then 100 g (0.8 mol) of 80% by weight sulfuric acid was slowly added thereto to provide a solution in which monomethyl sulfate was produced. Thereafter, 54.3 g of toluene, 150 g (1.4 mol) of ortho-cresol, and 5.5 g (0.03 mol) of dodecanethiol were added thereto, followed by setting the temperature in the separable flask to 30° C. In the dropping funnel, 73 g (0.5 mol) of 2-ethylhexanal was added, and it was slowly fed dropwise to the separable flask for 30 minutes. After completion of the dropwise addition of 2-ethylhexanal, the reaction was allowed to proceed at 30° C. for 2 hours. After completion of the reaction, 100.0 g of ethyl acetate and 100.0 g of demineralized water were fed, and the resulting mixture was mixed. Thereafter, the mixture was left to stand, and the aqueous phase in the lower layer, was extracted. Thereafter, saturated sodium hydrogen carbonate solution was added to the obtained organic phase to allow neutralization, followed by confirming that the pH of the aqueous phase in the lower layer, became not less than 9. After extraction of the aqueous phase in the lower layer, demineralized water was added to the obtained organic phase, and the resulting mixture was stirred for 10 minutes. Thereafter, the mixture was left to stand, and the aqueous phase was extracted. Part of the obtained organic phase was removed, and subjected to measurement using a high-performance liquid chromatograph-mass spectrometer. As a result, a mass number of 325 ($M^+$-1) was found in the negative mode, indicating production of 1,1-bis(4-hydroxy-3-methylphenyl)-2-ethylhexane. As a result of analysis using high-performance liquid chromatography, the production rate of 1,1-bis(4-hydroxy-3-methylphenyl)-2-ethylhexane was found to be 67.4% by area. For Examples 23 to 39, the aromatic alcohol, the ketone or the aldehyde, and the synthesized bisphenol are summarized in Table 8. As a result, it became clear that a variety of bisphenols can be synthesized by using a monoalkyl sulfate as a catalyst.

TABLE 8

| | | Structures of bisphenols synthesized using monoalkyl sulfate as catalyst | |
|---|---|---|---|
| Example | Aromatic alcohol | Ketone or aldehyde | Synthesized bisphenol |
| 23 | Ortho-cresol | Acetone | |
| 24 | Phenol | Acetone | |
| 25 | Phenol | Dodecanal | |
| 26 | Ortho-cresol | Dodecanal | |

TABLE 8-continued

Structures of bisphenols synthesized using monoalkyl sulfate as catalyst

| Example | Aromatic alcohol | Ketone or aldehyde | Synthesized bisphenol |
|---------|------------------|--------------------|-----------------------|
| 27 | Ortho-cresol | Fluorenone | |
| 28 | Ortho-cresol | Cyclohexanone | |
| 29 | Ortho-cresol | Cycloheptanone | |
| 30 | Ortho-cresol | Methyl ethyl ketone | |
| 31 | Ortho-cresol | Methyl isobutyl ketone | |
| 32 | 2,6-Xylenol | Acetone | |
| 33 | Phenol | 3,3,5-Trimethylcyclohexanone | |

TABLE 8-continued

Structures of bisphenols synthesized using monoalkyl sulfate as catalyst

| Example | Aromatic alcohol | Ketone or aldehyde | Synthesized bisphenol |
|---|---|---|---|
| 34 | Ortho-cresol | Acetophenone | (structure) |
| 35 | 2-Phenylphenol | Acetone | (structure) |
| 36 | 2-Cyclohexylphenol | Acetone | (structure) |
| 37 | 2-Benzylphenol | Acetone | (structure) |
| 38 | Phenol | 2-Ethylhexanal | (structure) |
| 39 | Ortho-cresol | 2-Ethylhexanal | (structure) |

Example 40

In a full-jacket type 1 L separable flask equipped with a thermometer, a stirrer, and a 100 mL dropping funnel, a cooling medium at −10° C. was allowed to flow through the jacket. Under a nitrogen atmosphere, 240 g of toluene, 9 g of methanol, and 172.5 g (1.60 mol) of ortho-cresol were added therein, and the internal temperature was decreased to −5° C. Thereafter, 67.5 g of 98% by weight sulfuric acid was added thereto. In the dropping funnel, a mixture of 4.1 g of dodecanethiol and 45.8 g (0.79 mol) of acetone was placed. When the internal temperature of the separable flask became −5° C., the mixture was slowly fed dropwise for 1 hour. After the dropwise feeding, the resulting mixture was stirred at 10° C. for 1 hour, and then the temperature was increased to 45° C., followed by stirring the mixture for 1 hour while maintaining the temperature at 45° C. To the resulting reaction liquid, 128 g of 28% by weight aqueous sodium hydroxide solution was added. While the temperature was increased to 80° C., 28% by weight aqueous sodium hydroxide solution was added thereto such that the pH is within the range of 5 to 8. When the internal temperature reached 80° C., the aqueous phase was extracted. This was followed by washing with saturated aqueous sodium bicarbonate and then with water. Part of the obtained organic phase was removed, and subjected to high-performance liquid chromatography to analyze the amount of bisphenol C produced. As a result, the reaction yield in terms of acetone was found to be 80 mol %.

Example 41

In a glass reaction vessel with a capacity of 150 mL equipped with a stirrer and a distillate tube, 100 g (0.39 mol) of the bisphenol C obtained in Example 9, 86.5 g (0.4 mol) of diphenyl carbonate, and 479 μL of 400 ppm by mass aqueous cesium carbonate solution were placed. The pressure in the glass reaction vessel was reduced to about 100 Pa, and then the pressure was restored to atmospheric pressure with nitrogen. By repeating this operation three times, the atmosphere in the reaction vessel was replaced with nitrogen. Thereafter, the reaction vessel was immersed in an oil bath at 200° C. to allow dissolution of the content. After setting the rotation speed of the stirrer to 100 revolutions per minute, the pressure in the reaction vessel was reduced from 101.3 kPa to 13.3 kPa in terms of the absolute pressure for 40 minutes while the phenol in the reaction vessel as a by-product of oligomerization reaction between bisphenol C and diphenyl carbonate was evaporated. Subsequently, while the pressure in the reaction vessel was kept at 13.3 kPa, and while the phenol was further evaporated, transesterification reaction was carried out for 80 minutes. Thereafter, the external temperature of the reaction vessel was increased to 250° C., and the pressure in the reaction vessel was reduced from 13.3 kPa to 399 Pa in terms of the absolute pressure for 40 minutes to remove the distilled phenol to the outside of the system. Thereafter, the external temperature of the reaction vessel was increased to 280° C., and the absolute pressure in the reaction vessel was reduced to 30 Pa, followed by performing polycondensation reaction. When the stirring power of the stirrer in the reaction vessel reached a predetermined level, the polycondensation reaction was stopped. Subsequently, the pressure in the reaction vessel was restored with nitrogen to 101.3 kPa in terms of the absolute pressure, and then the pressure was increased to 0.2 MPa in terms of the gauge pressure, followed by extracting a polycarbonate in a strand shape from the bottom of the reaction vessel, to obtain a polycarbonate resin having the strand shape. Thereafter, using a rotary cutter, the strand was pelletized to obtain a polycarbonate resin having a pellet shape.

The viscosity-average molecular weight (Mv) of the polycarbonate was 25,000. The pellet YI was 7.6.

INDUSTRIAL APPLICABILITY

By the present invention, a bisphenol composition suitable as a raw material for production of a polycarbonate resin, and a production method therefor are provided. Moreover, since the bisphenol composition of the present invention contains an aromatic alcohol sulfonate, melt polymerization reaction with a diester carbonate can be efficiently allowed to proceed to enable production of a polycarbonate resin having an excellent color tone.

What is claimed is:
1. A bisphenol composition comprising an aromatic alcohol sulfonate at not less than 0.1 ppb by mass with respect to a bisphenol.
2. The bisphenol composition according to claim 1, wherein, when a mixture of the bisphenol composition and diphenyl carbonate having a ratio of amounts of the diphenyl carbonate to the bisphenol of 1.1 is heated for 90 minutes on an aluminum block heater heated at 194° C., the phenol production rate in a reaction liquid obtained thereafter is not less than 0.3% by area.
3. The bisphenol composition according to claim 1, wherein the aromatic alcohol sulfonate contains a compound represented by General Formula (1) and/or General Formula (2):

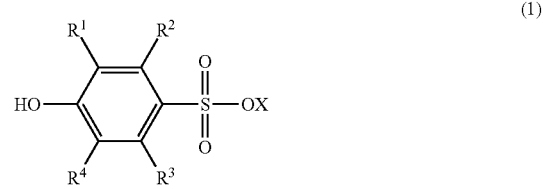

(1)

wherein $R^1$ to $R^4$ each independently represent a hydrogen atom, halogen atom, alkyl group, alkoxy group, or aryl group; and X represents a metal atom;

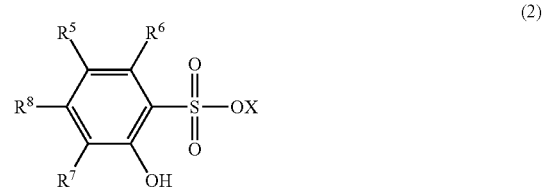

(2)

wherein $R^5$ to $R^8$ each independently represent a hydrogen atom, halogen atom, alkyl group, alkoxy group, or aryl group; and X represents a metal atom.
4. The bisphenol composition according to claim 3, wherein X in the General Formula (1) and/or the General Formula (2) represents a sodium atom or a potassium atom.
5. The bisphenol composition according to claim 1, wherein the content of the aromatic alcohol sulfonate with respect to the bisphenol is not more than 1.0% by mass.
6. The bisphenol composition according to claim 1, wherein the content of the bisphenol in the composition is not less than 95.0% by mass.
7. A method of producing a bisphenol composition, comprising reacting a ketone or an aldehyde with an aromatic alcohol in the presence of sulfuric acid to produce the bisphenol composition according to claim 1, wherein a reaction liquid used for the reaction contains an organic phase and an aqueous phase separated from each other and a monoalkyl sulfate is produced from reaction of sulfuric acid with an aliphatic alcohol and is contained in the aqueous phase.
8. A method of producing a polycarbonate resin by a transesterification reaction, comprising reacting the bisphenol composition according to claim 1 with a diester carbonate in the presence of an alkali metal compound and/or an alkaline earth metal compound to produce a polycarbonate resin.
9. A polycarbonate resin comprising an aromatic alcohol sulfonate at not less than 1 ppb by mass in a resin.
10. A method of producing a bisphenol, comprising a step of producing a bisphenol from reaction of an aromatic alcohol with a ketone or an aldehyde, wherein a reaction liquid used for the reaction contains an organic phase and an aqueous phase separated from each other, the aqueous phase containing a monoalkyl sulfate.

11. The method of producing a bisphenol according to claim 10, wherein the monoalkyl sulfate is produced from reaction of sulfuric acid with an aliphatic alcohol.

12. The method of producing a bisphenol according to claim 11, wherein the sulfuric acid and the aliphatic alcohol are mixed together to produce the monoalkyl sulfate, and then the monoalkyl sulfate is mixed with a reaction liquid containing an aromatic alcohol.

13. The method of producing a bisphenol according to claim 10, wherein the monoalkyl sulfate concentration in the aqueous phase is 0.0001% by mass to 50% by mass.

14. The method of producing a bisphenol according to claim 10, wherein the step of producing a bisphenol is carried out in the presence of a thiol.

15. The method of producing a bisphenol according to claim 14, wherein the thiol is mixed with the ketone or the aldehyde, followed by mixing with the monoalkyl sulfate.

16. A method of producing a polycarbonate resin, comprising producing a bisphenol by the method of producing a bisphenol according to claim 10, and then reacting the resulting bisphenol to produce a polycarbonate resin.

\* \* \* \* \*